US011536556B2

(12) United States Patent
Sonoda et al.

(10) Patent No.: US 11,536,556 B2
(45) Date of Patent: Dec. 27, 2022

(54) MEASUREMENT SUPPORT DEVICE, ENDOSCOPE SYSTEM, PROCESSOR FOR ENDOSCOPE SYSTEM, AND MEASUREMENT SUPPORT METHOD FOR MEASURING OBJECT SIZE

(71) Applicant: FUJIFILM Corporation, Tokyo (JP)

(72) Inventors: Shinichiro Sonoda, Kanagawa (JP); Takeichi Tatsuta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 938 days.

(21) Appl. No.: 16/297,734

(22) Filed: Mar. 11, 2019

(65) Prior Publication Data

US 2019/0204068 A1 Jul. 4, 2019

Related U.S. Application Data

(63) Continuation of application No. PCT/JP2017/028644, filed on Aug. 7, 2017.

(30) Foreign Application Priority Data

Sep. 15, 2016 (JP) .............................. JP2016-180808

(51) Int. Cl.
*G01B 11/02* (2006.01)
*A61B 1/06* (2006.01)
(Continued)

(52) U.S. Cl.
CPC .......... *G01B 11/02* (2013.01); *A61B 1/00009* (2013.01); *A61B 1/00045* (2013.01);
(Continued)

(58) Field of Classification Search
USPC ....................................................... 600/108
See application file for complete search history.

(56) References Cited

U.S. PATENT DOCUMENTS 4,290,667 A * 9/1981 Chown ................ G02B 6/3843
385/35
5,070,401 A * 12/1991 Salvati ................ G01B 11/024
702/159
(Continued)

FOREIGN PATENT DOCUMENTS

EP 1480067 11/2004
GB 1233604 5/1971
(Continued)

OTHER PUBLICATIONS

Machine language translation of JPH07136101 (May 1995).*
(Continued)

*Primary Examiner* — John P Leubecker
(74) *Attorney, Agent, or Firm* — JCIPRNET

(57) ABSTRACT

Provided are a measurement support device, an endoscope system, a processor for an endoscope system, and a measurement support method capable of easily and highly accurately measuring the size of a subject. In the measurement support device related to one aspect of the invention, the position of a spot by measurement auxiliary light is measured, and information indicating the actual size of a subject is acquired on the basis of the measurement result to create and display a marker. Moreover, an optical axis of the measurement auxiliary light has an inclination angle that is not 0 degrees with respect to an optical axis of the imaging optical system in a case where the optical axis of the measurement auxiliary light is projected on a plane including the optical axis of the imaging optical system.

17 Claims, 26 Drawing Sheets

(51) Int. Cl.
  *A61B 1/045* (2006.01)
  *G02B 3/00* (2006.01)
  *G02B 23/24* (2006.01)
  *A61B 5/107* (2006.01)
  *A61B 1/00* (2006.01)
  *A61B 5/06* (2006.01)
  *G01B 11/14* (2006.01)

(52) U.S. Cl.
  CPC ........ *A61B 1/00096* (2013.01); *A61B 1/0661* (2013.01); *A61B 5/064* (2013.01); *A61B 5/1076* (2013.01); *A61B 5/1079* (2013.01); *G01B 11/14* (2013.01); *G02B 3/00* (2013.01); *G02B 23/24* (2013.01); *A61B 1/045* (2013.01); *A61B 2562/0242* (2013.01)

(56) References Cited

U.S. PATENT DOCUMENTS

| | | | |
|---|---|---|---|
| 5,436,655 A | 7/1995 | Hiyama et al. | |
| 5,669,871 A * | 9/1997 | Sakiyama | G01B 11/25 348/136 |
| 5,677,536 A * | 10/1997 | Vickers | G01T 1/1642 250/252.1 |
| 6,283,483 B1 * | 9/2001 | Johnson | B62D 9/00 280/5.522 |
| 8,724,015 B2 | 5/2014 | Yoshino | |
| 2001/0016096 A1 * | 8/2001 | Feldman | G02F 1/31 385/11 |
| 2002/0136498 A1 * | 9/2002 | Aldridge | G02B 6/3897 385/39 |
| 2004/0242961 A1 | 12/2004 | Bughici et al. | |
| 2010/0105980 A1 | 4/2010 | Shimizu et al. | |
| 2010/0324366 A1 | 12/2010 | Shimotsu | |
| 2013/0194404 A1 * | 8/2013 | Christiansen | A61B 1/00009 348/67 |
| 2015/0222801 A1 * | 8/2015 | Kresser | G03B 17/54 348/362 |
| 2015/0373243 A1 * | 12/2015 | Toda | H01L 27/156 348/294 |
| 2017/0189108 A1 * | 7/2017 | Melsky | A61B 18/082 |

FOREIGN PATENT DOCUMENTS

| | | |
|---|---|---|
| JP | S59068318 | 5/1984 |
| JP | S62049208 | 3/1987 |
| JP | S62073223 | 4/1987 |
| JP | H03231622 | 10/1991 |
| JP | H05042097 | 2/1993 |
| JP | H07136101 | 5/1995 |
| JP | H08201026 | 8/1996 |
| JP | H08285541 | 11/1996 |
| JP | 2002156212 | 5/2002 |
| JP | 2002336188 | 11/2002 |
| JP | 3446272 | 9/2003 |
| JP | 2008122759 | 5/2008 |
| JP | 2010063485 | 3/2010 |
| JP | 2011000258 | 1/2011 |
| JP | 2012039255 | 2/2012 |
| JP | 2016106867 | 6/2016 |

OTHER PUBLICATIONS

"Office Action of Japan Counterpart Application," with English translation thereof, dated Jan. 21, 2020, p. 1-p. 10.
"International Search Report (Form PCT/ISA/210) of PCT/JP2017/028644," dated Oct. 31, 2017, with English translation thereof, pp. 1-5.
"Written Opinion of the International Searching Authority (Form PCT/ISA/237) of PCT/JP2017/028644," dated Oct. 31, 2017, with English translation thereof, pp. 1-15.
"Search Report of Europe Counterpart Application", dated Aug. 16, 2019, p. 1-p. 10.
"Office Action of Japan Counterpart Application", dated Aug. 13, 2020, with English translation thereof, pp. 1-8.
"Office Action of Japan Counterpart Application" with English translation thereof, dated Apr. 26, 2021, p. 1-p. 27.

* cited by examiner x (X-DIRECTION PIXEL POSITION OF SPOT)

FIG. 28
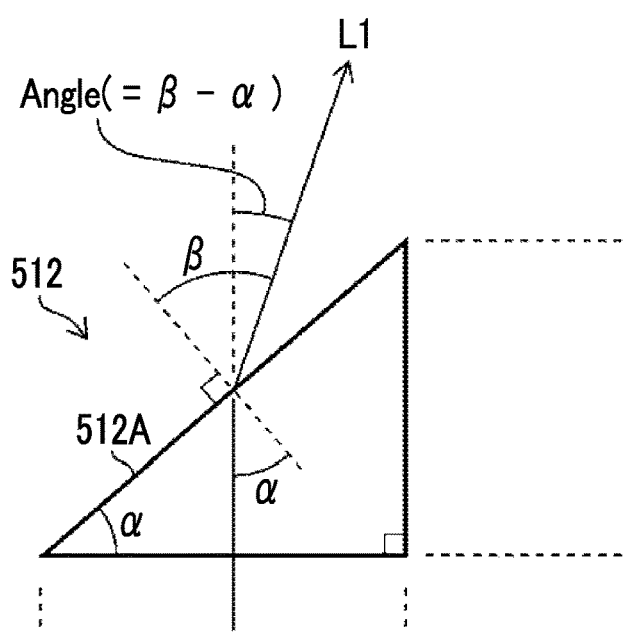
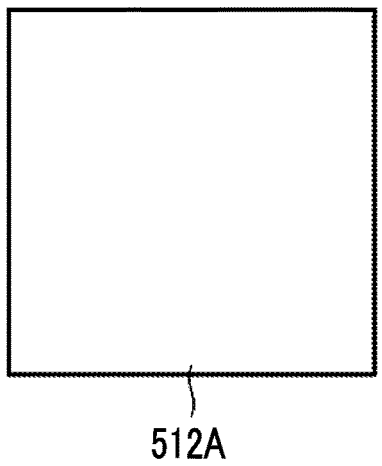

FIG. 29

| | dcl (mm) | zn (mm) | zf (mm) | θ (deg) | Z1 (mm) | Z1a | Z2 (mm) | Z2a | a (mm) | b (mm) | Material | n | Angle (deg) | α (deg) | Z1a × Z2a | EVALUATION |
|---|---|---|---|---|---|---|---|---|---|---|---|---|---|---|---|---|
| EXAMPLE 1 | 2 | 2 | 100 | 140 | 48.9 | 0.18 | -0.98 | -0.18 | 3.93 | 96.07 | BK7 | 1.5145 | 27.0 | 36.0 | -0.031807 | VERY EXCELLENT |
| EXAMPLE 2 | 2 | 1.5 | 20 | 140 | 12.3 | 0.22 | -0.93 | -0.22 | 2.80 | 17.20 | BK7 | 1.5145 | 35.6 | 39.7 | -0.050377 | VERY EXCELLENT |
| EXAMPLE 3 | 2 | 2 | 100 | 170 | 49.1 | 0.04 | -0.98 | -0.04 | 3.91 | 96.09 | BK7 | 1.5145 | 27.1 | 36.1 | -0.001838 | VERY EXCELLENT |
| EXAMPLE 4 | 2 | 1.5 | 20 | 170 | 12.3 | 0.05 | -0.92 | -0.05 | 2.79 | 17.21 | BK7 | 1.5145 | 35.6 | 39.7 | -0.002911 | VERY EXCELLENT |
| EXAMPLE 5 | 1 | 2 | 100 | 170 | 0.0 | 0.00 | -0.98 | -0.04 | 100.00 | 0.00 | BK7 | 1.5145 | 1.1 | 2.2 | 0.000000 | EXCELLENT |
| EXAMPLE 6 | 5 | 1.5 | 20 | 170 | 228.6 | 1.00 | 12.52 | 0.73 | 0.43 | 19.57 | - | - | 77.9 | - | 0.730243 | NO GOOD |
| EXAMPLE 7 | 5 | 1.5 | 20 | 170 | 107.4 | 0.47 | 3.43 | 0.20 | 0.89 | 19.11 | TiO2 | 2.493 | 66.0 | 23.6 | 0.094114 | NO GOOD |
| EXAMPLE 8 | 1 | 1.5 | 20 | 140 | 0.0 | 0.00 | -0.93 | -0.22 | 20.00 | 0.00 | BK7 | 1.5145 | 5.7 | 10.8 | 0.000000 | EXCELLENT |
| EXAMPLE 9 | 5 | 1.5 | 20 | 140 | 54.9 | 1.00 | -0.50 | -0.12 | 1.67 | 18.33 | TiO2 | 2.493 | 50.2 | 22.5 | -0.122242 | VERY EXCELLENT |
| EXAMPLE 10 | 1 | 2 | 100 | 140 | 8.2 | 0.03 | -0.82 | -0.15 | 10.82 | 89.18 | BK7 | 1.5145 | 10.5 | 18.9 | -0.004450 | VERY EXCELLENT |
| COMPARATIVE EXAMPLE | 2 | 2 | 100 | 140 | -2.0 | -0.01 | -2.00 | -0.36 | - | - | BK7 | 1.5145 | 0.0 | 0.0 | 0.002650 | NO GOOD |

MEASUREMENT SUPPORT DEVICE, ENDOSCOPE SYSTEM, PROCESSOR FOR ENDOSCOPE SYSTEM, AND MEASUREMENT SUPPORT METHOD FOR MEASURING OBJECT SIZE

CROSS-REFERENCE TO RELATED APPLICATIONS

The present application is a Continuation of PCT International Application No. PCT/JP2017/028644 filed on Aug. 7, 2017 claiming priority under 35 U.S.C § 119(a) to Japanese Patent Application No. 2016-180808 filed on Sep. 15, 2016. Each of the above applications is hereby expressly incorporated by reference, in their entirety, into the present application.

BACKGROUND OF THE INVENTION

1. Field of the Invention

The present invention relates to a measurement support device, an endoscope system, a processor for an endoscope system, and a measurement support method, and particularly, to a measurement support device, a processor for an endoscope system, and a measurement support method that measures the size of a test object using measurement auxiliary light, an endoscope system.

2. Description of the Related Art

In the field of measurement devices for endoscopes or the like, measuring the distance to a test object or calculating the length and the size of the test object is performed. For example, JP2008-122759A discloses that a subject distance is measured by a stereoscopic camera, and the size of a mark serving as a rough standard of the size of a subject is calculated on the basis of the subject distance and the visual field angle of an endoscope, and the mark is described together with an image of the subject, and the size of the subject can be known from this mark.

Additionally, JP1996-285541A (JP-H08-285541A) discloses a technique of finding a subject distance by using measurement auxiliary light. In JP1996-285541A, an irradiation surface is observed by radiating a laser beam from the optical fiber. Then, by utilizing the fact a radiation point of the laser beam is brought close to or separated from the center of a visual field depending on the distance from the optical fiber to the irradiation surface and by correcting the amount of deviation in advance, the subject distance can be known from the amount of deviation.

SUMMARY OF THE INVENTION

However, in the above-described JP2008-122759A, in order to measure the distance with the stereoscopic camera, two cameras are required, and a distal end part of the endoscope increases. Therefore, a burden to the test object is large. Moreover, since the distance measurement is performed and the size of the mark is calculated on the basis of the result, processing is complicated.

Additionally, the technique disclosed in JP1996-285541A is for performing the distance measurement, the processing is complicated, and the length and the size of the subject cannot be directly found. Moreover, the laser beam is radiated parallel to an optical axis of an imaging optical system. Thus, in a case where the observation distance is short (in a case where the subject is present in a location close to a distal end of the endoscope), there is a problem that the laser beam may deviate from the visual field of the imaging optical system and measurement cannot be performed. Moreover, there is a problem that the sensitivity of a position change of the spot to a change in the subject distance is low, and measurement accuracy is low. Moreover, since observation light is radiated as it is from a distal end of an optical fiber, there is a problem that the beam may spread with the distance, and spot diameter may increase, the visual recognition of the spot may is difficult, and the measurement accuracy may deteriorate in a case where the observation distance is long.

In this way, in the related-art technique, the size (length) of the subject cannot be easily and highly accurately measured.

The invention has been made in view of such circumstances, and an object thereof is to provide a measurement support device, an endoscope system, a processor for an endoscope system, and a measurement support method capable of easily and highly accurately measuring the size of a subject.

In order to achieve the above-described object, a measurement support device related to a first aspect of the invention comprises a head including a collimator that emits measurement auxiliary light emitted from a light source as a parallel beam; an imaging unit that acquires an image of a subject, on which a spot is formed with the measurement auxiliary light emitted from the head, via an imaging optical system and an imaging element; a measurement unit that measures a position of the spot on the imaging element on the basis of the image of the subject; a storage unit that stores information indicating a relationship between the position of the spot on the imaging element and an actual size of the subject; a marker creation unit that acquires the information indicating the relationship from the storage unit on the basis of the measured position of the spot and creates a marker indicating the actual size on the basis of the acquired information; and a display control unit that makes a display device display the image of the subject on which the spot is formed and the marker, and the marker be displayed in the vicinity of the spot in the image of the subject, the head emits measurement auxiliary light of which an optical axis has an inclination angle that is not 0 degrees with respect to an optical axis of the imaging optical system, and crosses a field angle of the imaging optical system, in a case where the optical axis of the measurement auxiliary light is projected on a plane including the optical axis of the imaging optical system. In the first aspect, since the marker indicating the actual size of the subject is displayed together with the image of the subject, a user can easily measure the size of the subject by comparing the subject (object to be measured) with the marker. In addition, in the first aspect, a specific value of the "actual size" can be set in accordance with conditions, such as the type of subject and the purposes of measurement.

In the first aspect, since the measurement auxiliary light is collimated light, a beam diameter and a spot diameter are small, marking to the subject (object to be measured) is easy, and position measurement accuracy is high. Moreover, even in a case where the observation distance is long, there is almost no spread of a beam, and highly-accurate measurement can be performed. Additionally, since the position of the spot is measured, the information stored in the storage unit is acquired on the basis of the measurement result to create and display the marker, there is no need for distance measurement unlike the above-described JP2008-122759A and JP1996-285541A, device configuration is simple, and the measurement is easy.

Additionally, the optical axis of the measurement auxiliary light has the inclination angle, which is not 0 degrees with respect to the optical axis of the imaging optical system, and crosses the field angle of the imaging optical system in a case where the optical axis of the measurement auxiliary light is projected on the plane including the optical axis of the imaging optical system. Thus, by setting the inclination angle appropriately, the measurement auxiliary light can enter the visual field of the imaging optical system even in a case where the observation distance is short. Moreover, since the optical axis of the measurement auxiliary light has the inclination angle that is not 0 degrees with respect to the optical axis of the imaging optical system in a case where the optical axis of the measurement auxiliary light is projected on the plane including the optical axis of the imaging optical system, the sensitivity of a change in the position of the spot to a change in the observation distance is high, and the measurement accuracy is high.

In this way, in the measurement support device related to the first aspect, the size of the subject can be easily and highly accurately measured similarly to the first aspect.

In the first aspect, "the information indicating the relationship between the dimension of the subject on the imaging element and the actual size of the subject" can be acquired, for example, by imaging a figure for measurement on which patterns corresponding to the actual size are regularly recorded. Additionally, in the first aspect, the marker is displayed "in the vicinity of" the spot. However, the center of the marker may be displayed in alignment with the center of the spot, or the marker may be displayed on a position apart from the spot. In the first aspect, laser light, LED light, or the like can be used as the measurement auxiliary light.

In the measurement support device related to a second aspect based on the first aspect, the optical axis of the measurement auxiliary light emitted from the head is present in the plane (the plane including the optical axis of the imaging optical system). The second aspect defines one aspect of the relationship between a direction of the optical axis of the imaging optical system and a direction of the optical axis of the measurement auxiliary light. Since the optical axis of the imaging optical system and the optical axis of the measurement auxiliary light are present on the same plane and a track of the marker passes through the center of a screen, a region where the marker is present in the vicinity of the center of the screen becomes wide, and the measurement accuracy is improved.

In the measurement support device related to a third aspect based on the first and second aspects, the optical axis of the measurement auxiliary light emitted from the head intersects the optical axis of the imaging optical system in the plane (the plane including the optical axis of the imaging optical system). According to the third aspect, since the relationship between the direction of the optical axis of the imaging optical system and the direction of the optical axis of the measurement auxiliary light is more specifically defined and the relationship between the optical axes becomes simple, processing is easy. In addition, in the third aspect, it is preferable to set the above-described inclination angle such that an intersection position between the optical axes is present between the near end and the far end of the observation distance range. The reason why it is preferable to set the inclination angle in this way is as follows. That is, the distortion aberration increases depending on the configuration of the imaging optical system. In that case, it is preferable to perform measurement not at a peripheral portion of an image but at a central portion of the image. However, by setting the inclination angle as described above, it is possible to perform measurement at the central portion of the image.

In the measurement support device related to any one of a fourth aspect based on any one of the first to third aspects, the head has an optical member that changes an emission direction of the measurement auxiliary light emitted from the collimator and that changes the emission direction of the measurement auxiliary light such that an angle formed in the plane between the optical axis of the measurement auxiliary light emitted by the head and the optical axis of the imaging optical system becomes the inclination angle. According to the fourth aspect, since the emission direction of the measurement auxiliary light is changed by the optical member, the head can be disposed straight (parallel to the optical axis of the imaging optical system), and a distal end portion of the measurement support device can be downsized (reduced in diameter).

In the measurement support device related to a fifth aspect based on the fourth aspect, the optical member is a prism member having an apex angle depending on the inclination angle. The fifth aspect defines one aspect of the optical member that changes the emission direction of the measurement auxiliary light.

The measurement support device related to a sixth aspect based on any one the first to fifth aspects further comprises an optical fiber that allows the measurement auxiliary light emitted from the light source to propagate to the collimator in a single transverse mode. According to the sixth aspect, the optical fiber propagates the measurement auxiliary light in the single transverse mode, a small-diameter clear spot can be formed. Accordingly, highly-accurate measurement can be performed.

In the measurement support device related to a seventh aspect based on any one of the first to sixth aspects based, the collimator is a graded index type lens of which a refractive index is highest on an optical axis thereof and decreases radially outward. According to the seventh aspect, since the collimator is the graded index type lens, a module that emits the measurement auxiliary light can be downsized (reduced in diameter).

In the measurement support device related to an eighth aspect based on any one of the first to seventh aspects, the collimator is a graded index type optical fiber of which a refractive index is highest on an optical axis thereof and decreases radially outward. According to the eighth aspect, since the collimator is the graded index type optical fiber, a module that emits the measurement auxiliary light can be downsized (reduced in diameter).

In the measurement support device related to a ninth aspect based on any one of the first to eighth aspects, the inclination angle is 1.1 degrees or more and 50.2 or less in a case where the optical axis of the measurement auxiliary light is projected on the plane. In a case where the inclination angle is a range defined in the ninth aspect, the intersection position between the optical axis of the imaging optical system and the optical axis of the measurement auxiliary light is present between the near end and the far end of the observation distance range (including the near end and the far end), measurement can be highly accurately performed at an image central portion where the influence of the distortion aberration of the imaging optical system is little. In addition, in the ninth aspect, it is more preferable that the inclination angle is 10.5 degrees or more and 50.2 or less.

This is because, in a case where the inclination angle is within this range, measurement can be performed in a portion closer to an image center and highly-accurate measurement can be performed.

In order to achieve the above-described object, the endoscope system related to the tenth aspect of the invention includes the measurement support device according to any one of the first to ninth aspects. Since the endoscope system related to the tenth aspect includes the measurement support device related to any one of the first to ninth aspects, the size of the subject can be easily and highly accurately measured.

The endoscope system related to an eleventh aspect based on the tenth aspect further comprises an endoscope having an insertion part to be inserted into a test object, the insertion part having a distal end rigid part and a bent part connected to a proximal end side of the distal end rigid part, and a soft part connected to a proximal end side of the bent part, and an operating part connected to a proximal end side of the insertion part, and the distal end rigid part is provided with the collimator and an imaging lens for forming an optical image of the spot on the imaging element. The eleventh aspect defines one aspect of the configuration of the distal end rigid part of the endoscope.

The endoscope system related to a twelfth aspect based on the tenth or eleventh aspect further comprises further comprises an illumination light source that radiates illumination light; and a control unit that controls illuminance of the illumination light, and the control unit makes the illuminance of the illumination light in a measurement mode in which an image of the spot is acquired by the imaging unit lower than that in a normal observation mode in which the subject is observed by irradiating the subject with the illumination light. In a case where the illuminance of the illumination light in imaging the spot is too high, there is a case where the contrast between the spot and portions other than the spot becomes small in an obtained image, recognition of the spot cannot be performed, and measurement becomes impossible. However, in the twelfth aspect, in the measurement mode in which the image of the spot is acquired by the imaging unit, the control unit makes the illuminance of illumination light lower than a normal observation mode in which the test object is irradiated with the illumination light so as to observe the test object. Thus, an image with a clear spot can be captured. Accordingly, highly-accurate measurement can be performed. In addition, in the twelfth aspect, how much the illuminance of the illumination light is lowered in the measurement mode may be set in accordance with the type, size, brightness, and the like of the test object, or the illumination light may be turned off as needed.

In the endoscope system related to a thirteenth aspect based on any one of the tenth to twelfth aspects, the imaging element is a color imaging element including a plurality of pixels including a plurality of two-dimensionally arranged light receiving elements, and color filters of a plurality of filter colors disposed in the plurality of pixels, and the measurement unit measures the position of the spot on the imaging element on the basis of an image created by an image signal of a pixel in which a color filter of a filter color with the highest sensitivity to a wavelength of the measurement auxiliary light, among the plurality of filter colors, is disposed. According to the thirteenth aspect, the position on the imaging element of the spot is measured on the basis of the image created by the image signal that is the pixel in which that the color filter of the filter color with the highest sensitivity to the wavelength of the measurement auxiliary light among the plurality of filter colors is disposed. Thus, an image with a clear spot can be imaged. Accordingly, highly-accurate measurement can be performed.

In order to achieve the above-described object, the processor related to a fourteen aspect of the invention is a processor for the endoscope system related to any one of the tenth to thirteenth aspects, and the processor comprises a light source drive unit that drives the light source, the measurement unit, the storage unit, the marker creation unit, and the display control unit. According to the fourteenth aspect, the size of the subject can be easily and highly accurately measured similarly to the first aspect. In the aspect of the fourteenth aspect, the light source of the measurement auxiliary light is disposed, for example, within a scope (proximal operating part of the endoscope) and is mounted on an electric circuit substrate part of the scope, and turn-on, turn-off, and the intensity of light is controlled in accordance with the electrical signals from the processor (light source drive unit).

In the processor related to the fifteenth aspect based on the fourteenth aspect, the light source drive unit is a laser drive unit that drives the laser light source.

In order to achieve the above-described object, a measurement support method related to a sixteenth aspect of the invention is a measurement support method using a measurement support device including a head including a collimator that emits measurement auxiliary light emitted from a light source as a parallel beam, an imaging unit that acquires an image of a subject, on which a spot is formed with the measurement auxiliary light, via an imaging optical system and an imaging element, and a storage unit that stores information indicating a relationship between a position of the spot on the imaging element and an actual size of the subject. The method comprises an auxiliary light emission step of emitting the measurement auxiliary light such that an optical axis of the auxiliary light has an inclination angle that is not 0 degrees with respect to an optical axis of the imaging optical system in a case where an optical axis of the measurement auxiliary light emitted from the head is projected on a plane including the optical axis of the imaging optical system; an imaging step of acquiring an image of the subject, on which the spot is formed with the measurement auxiliary light, via the imaging unit; a measuring step of measuring the position of the spot on the imaging element on the basis of the image of the subject; a marker creation step of acquiring the information indicating the relationship from the storage unit on the basis of the measured position of the spot and creating a marker indicating the actual size on the basis of the acquired information; and a display control step of making a display device display the image of the subject on which the spot is formed and the marker, and the marker be displayed in the vicinity of the spot in the image of the subject. According to the sixteenth aspect, the size of the subject can be easily and highly accurately measured similarly to the first aspect.

As described above, according to the measurement support device, the endoscope system, the processor for an endoscope system, and the measurement support method in the invention, the size of the subject can be easily and highly accurately measured.

BRIEF DESCRIPTION OF THE DRAWINGS

FIG. 28 is another view illustrating the definition of parameters in an example of the invention.

FIG. 29 is a table illustrating evaluation results of examples of the invention, and a comparative example.

DESCRIPTION OF THE PREFERRED EMBODIMENTS

Hereinafter, embodiments of a measurement support device, an endoscope system, a processor for an endoscope system, and a measurement support method related to the invention will be described in detail, referring to the accompanying drawings.

First Embodiment

Figure 1:
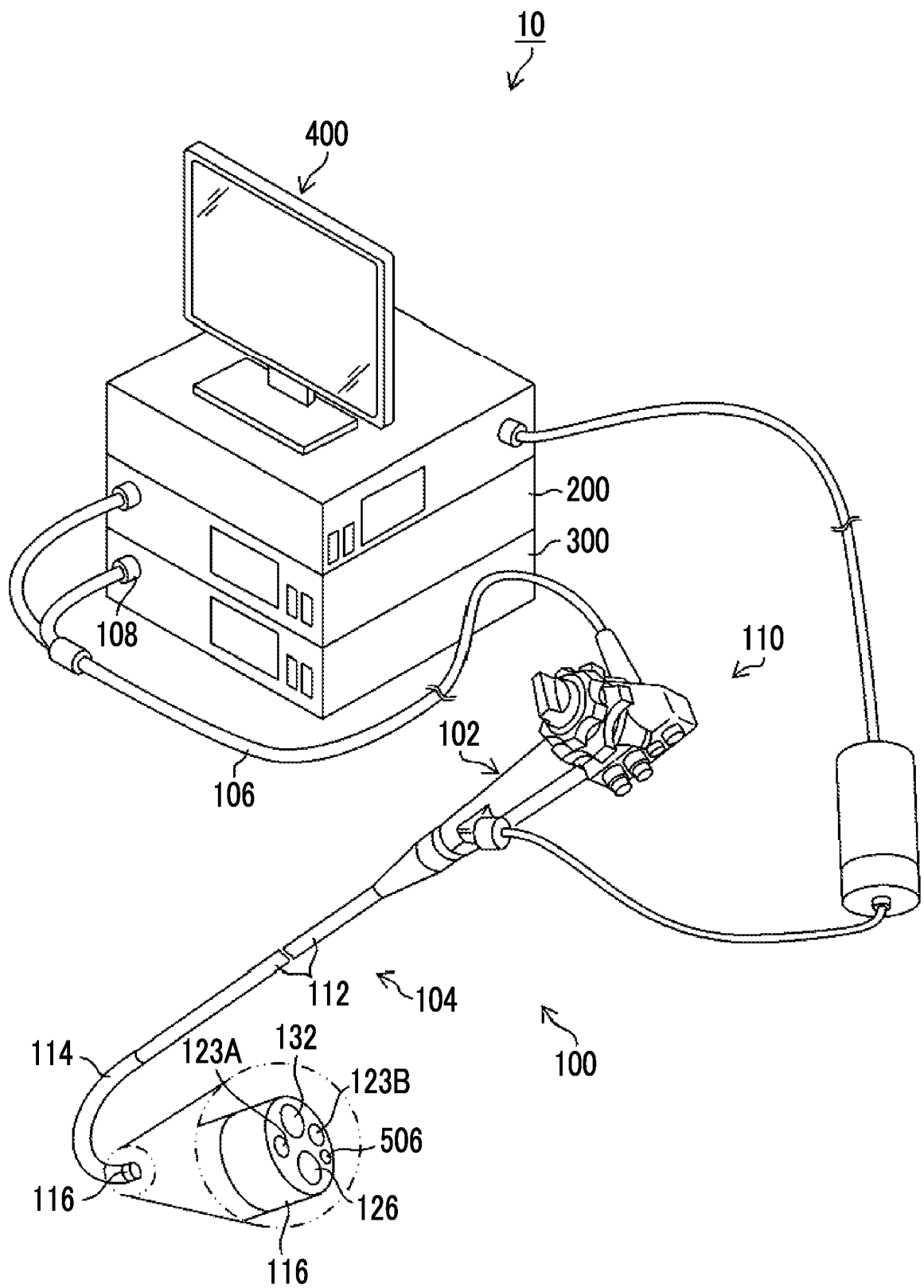
FIG. 1 is a view illustrating an overall configuration of an endoscope system related to a first embodiment of the invention.
Figure 2:
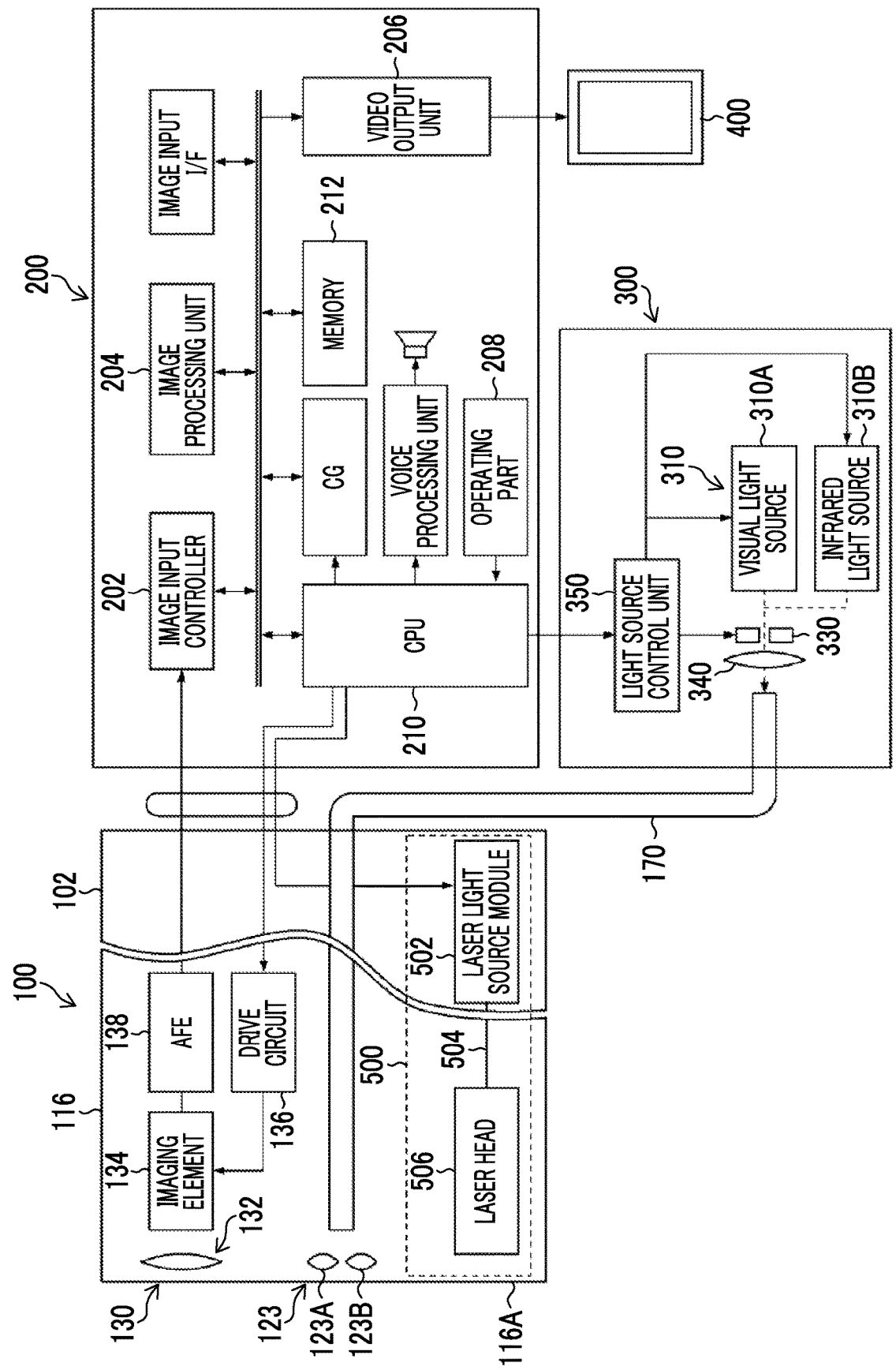
FIG. 2 is a block diagram illustrating the configuration of the endoscope system related to the first embodiment of the invention.

FIG. 1 is an external view illustrating an endoscope system 10 (a measurement support device, an endoscope system, and a processor for an endoscope system) related to a first embodiment, and FIG. 2 is a block diagram illustrating the configuration of main parts of the endoscope system 10. As illustrated in FIGS. 1 and 2, the endoscope system 10 includes an endoscope device 100 constituted of an endoscope body 110 (endoscope), an endoscope processor 200 (processor for an endoscope system), a light source device 300, and a monitor 400.

<Configuration of Endoscope Body>

The endoscope body 110 includes a proximal operating part 102 (operating part), and an insertion part 104 (insertion part) consecutively installed at the proximal operating part 102. An operator grips and operates the proximal operating part 102, and performs observation by inserting the insertion part 104 into the body of a test object. The insertion part 104 is constituted of a soft part 112 (soft part), a bent part 114 (bent part), and a distal end rigid part 116 (distal end rigid part) sequentially from the proximal operating part 102 side. The distal end rigid part 116 is provided with an imaging optical system 130 (imaging unit), an illumination unit 123, a forceps port 126, and a laser module 500, and the like (refer to FIGS. 1 to 3).

During observation or treatment, visible light, infrared light, or both can be radiated from illuminating lenses 123A and 123B of the illumination unit 123 by the operation of an operating part 208 (refer to FIG. 2). Additionally, washing water is released from a water supply nozzle (not illustrated) by the operation of the operating part 208, so that an imaging lens 132 (imaging lens) of the imaging optical system 130 and the illuminating lenses 123A and 123B can be washed. A pipe line (not illustrated) communicates with the forceps port 126 that opens at the distal end rigid part 116, and a treatment tool (not illustrated) for tumor removal or the like is inserted through to the pipe line is appropriately moved forward and backward so as to perform treatment required for the test object.

Figure 3:
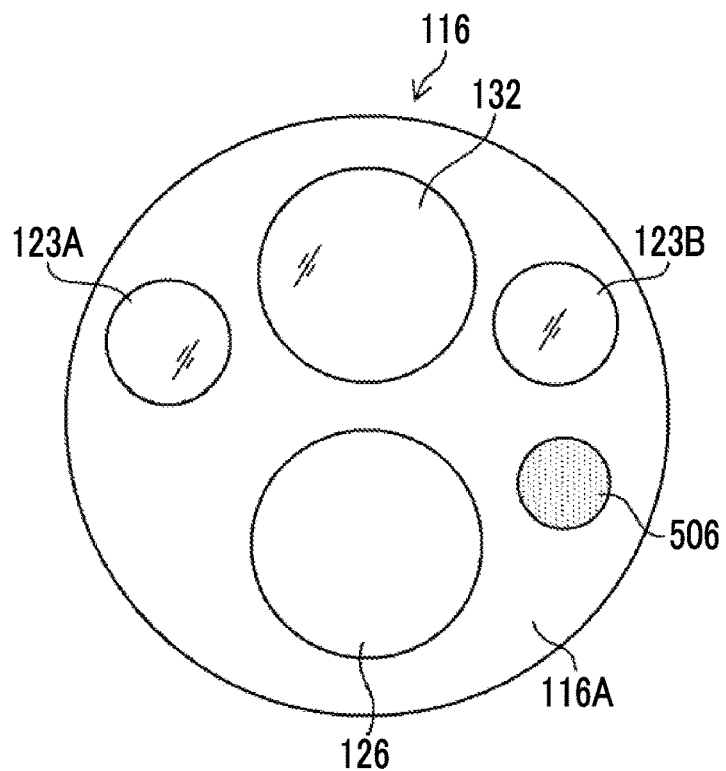
FIG. 3 is a view illustrating the configuration of a distal-end-side end surface of a distal end rigid part.

As illustrated in FIGS. 1 to 3, the imaging lens 132 is disposed on a distal-end-side end surface 116A of the distal end rigid part 116, and a complementary metal oxide semiconductor (CMOS) type imaging element 134 (an imaging element or a color imaging element), a drive circuit 136, and an analog front end (AFE) 138 are disposed at the back of the imaging lens 132 so as to output image signals. The imaging element 134 is a color imaging element, and includes a plurality of pixels constituted of a plurality of light receiving elements arranged in a matrix (two-dimensional array) in a specific pattern array (a Bayer array, a G-stripe R/B perfect checker, an X-Trans (registered trademark) array, a honeycomb array, or the like). Each pixel includes a microlens, a red (R), green (G), or blue (B) color filter, and a photoelectric conversion part (photodiode or the like). The imaging optical system 130 may create a color image from pixel signals of three colors of red, green, and blue, or may create an image from pixel signals of any one color or two colors among red, green, and blue.

In addition, in the first embodiment, a case where the imaging element 134 is a CMOS type imaging element is described. However, the imaging element 134 may be of charge coupled device (CCD) type.

An image of the test object (a tumor region or an affected region) or an optical image of a spot (to be described below) is formed on a light-receiving surface (imaging surface) of the imaging element 134 by the imaging lens 132, is converted into electrical signals, is output to the endoscope processor 200 via a signal cable (not illustrated), and is converted into video signals. Accordingly, observation images (refer to FIGS. 16 to 20) and the like are displayed on the monitor 400 connected to the endoscope processor 200.

Additionally, the illuminating lenses 123A (for visible light) and 123B (for infrared light) of the illumination unit 123 are provided adjacent to the imaging lens 132 on the distal-end-side end surface 116A of the distal end rigid part 116. An exit end of a light guide 170 to be described below is disposed at the back of the illuminating lenses 123A and 123B, the light guide 170 is inserted through the insertion part 104, the proximal operating part 102, and a universal cable 106, and an incident end of the light guide 170 is disposed within a light guide connector 108.

Figure 4:
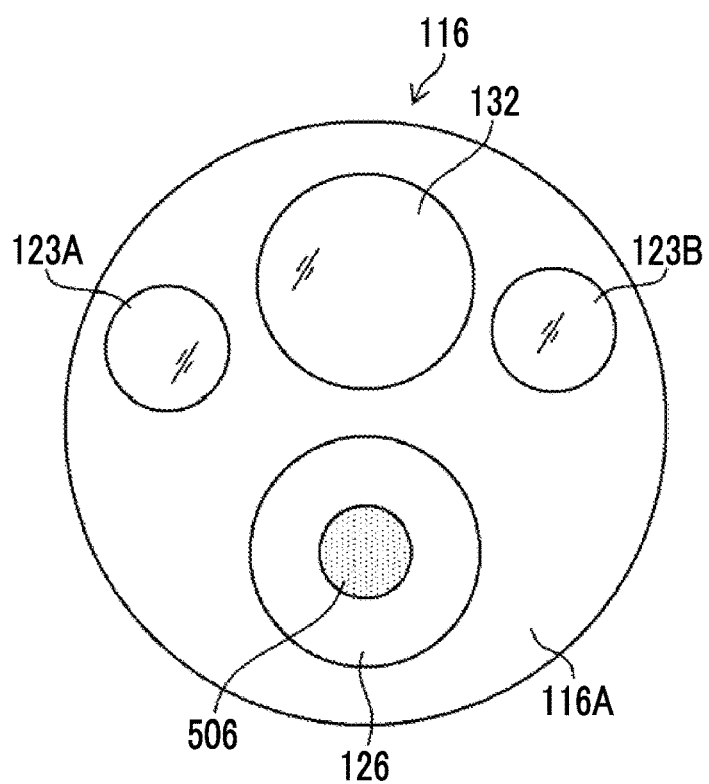
FIG. 4 is a view illustrating another configuration of the distal-end-side end surface of the distal end rigid part.

The distal-end-side end surface 116A is further provided with a laser head 506 (head) of the laser module 500 and is irradiated with spot light (measurement auxiliary light) via a prism 512 (prism member). The configuration of the laser module 500 will be described below. In addition, in the first embodiment, as illustrated in FIG. 3, the laser head 506 is provided separately from the forceps port 126. In the measurement support device and the endoscope system related to the invention, as illustrated in FIG. 4, the laser head 506 may be removably inserted through the pipe line (not illustrated) that communicates with the forceps port 126 opening at the distal end rigid part 116. In this case, it is not necessary to provide a pipe line dedicated to the laser head 506, and the pipe line with that communicates with the forceps port 126 can be shared with other treatment tools.

<Configuration of Laser Module>

Figure 5:
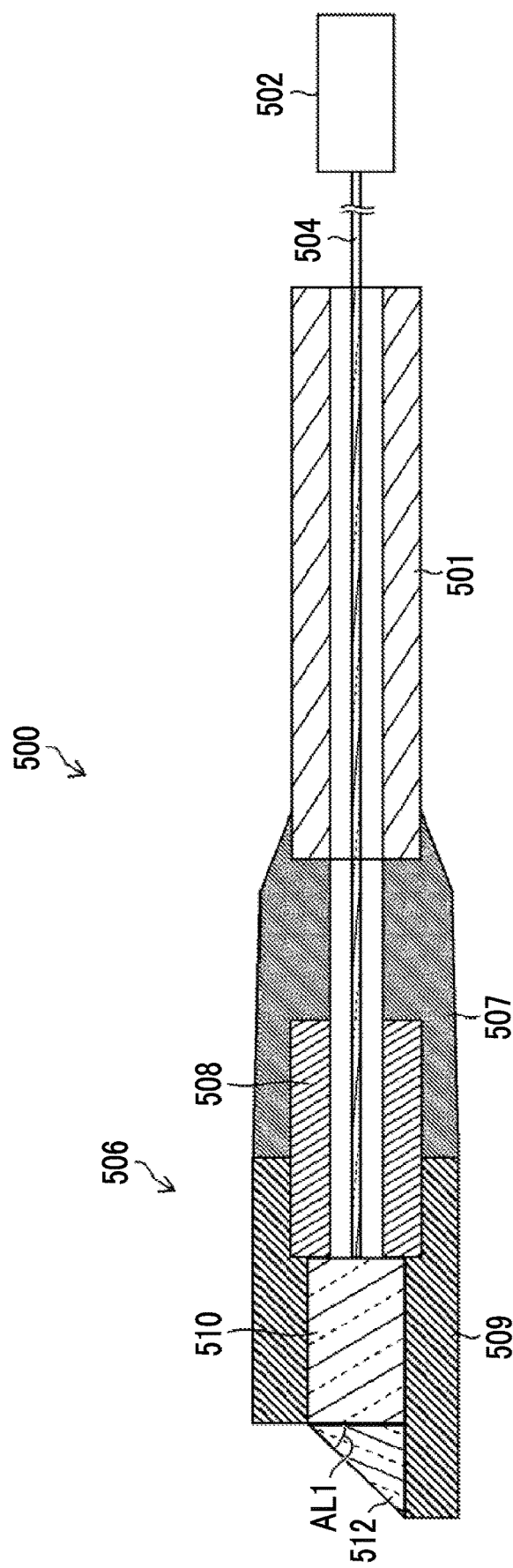
FIG. 5 is a view illustrating the configuration of a laser module.

As illustrated in FIGS. 2 and 5, the laser module 500 includes a laser light source module 502 (a light source or a laser light source), an optical fiber 504 (optical fiber), and the laser head 506 (head). A proximal end side (laser light source module 502 side) of the optical fiber 504 is covered with a fiber outer jacket 501, a distal end side (a side from which laser light is emitted) thereof is inserted into a ferrule 508 and is bonded with an adhesive, and an end surface is ground. A graded index (GRIN) lens 510 (a collimator or a graded index type lens) is mounted on a distal end side of the ferrule 508, and a prism 512 is mounted on a distal end side of the GRIN lens 510 so as to form a joined body. The ferrule 508 is a member for holding and connecting the optical fiber 504, and a hole for allowing the optical fiber 504 to be inserted therethrough is made empty in an axial direction (leftward-rightward direction of FIG. 5) at a central portion of the ferrule. A reinforcing member 507 is provided outside the ferrule 508 and the fiber outer jacket 501 to protect an optical fiber 504 or the like. The ferrule 508, the GRIN lens 510, and the prism 512 are housed in a housing 509 and is integrated with the reinforcing member 507 and the fiber outer jacket 501 to constitute the laser head 506.

In the laser head 506, for example, one having a diameter of 0.8 mm to 1.25 mm can be used as the ferrule 508. In addition, a fine-diameter ferrule is more preferable for downsizing. By virtue of the above-described configuration, the total diameter of the laser head 506 can be 1.0 mm to 1.5 mm.

The laser module 500 configured in this way is mounted on the insertion part 104. Specifically, as illustrated in FIG. 2, the laser light source module 502 is disposed at the portion of the proximal operating part 102 (scope) and is mounted on an electric circuit substrate part. Meanwhile, the laser head 506 is provided at the distal end rigid part 116, and the optical fiber 504 guides the laser light from the laser light source module 502 to the laser head 506. In addition, the laser light source module 502 may be provided within the light source device 300 so as to guide the laser light to the distal end rigid part 116 with the optical fiber 504.

Figure 6:
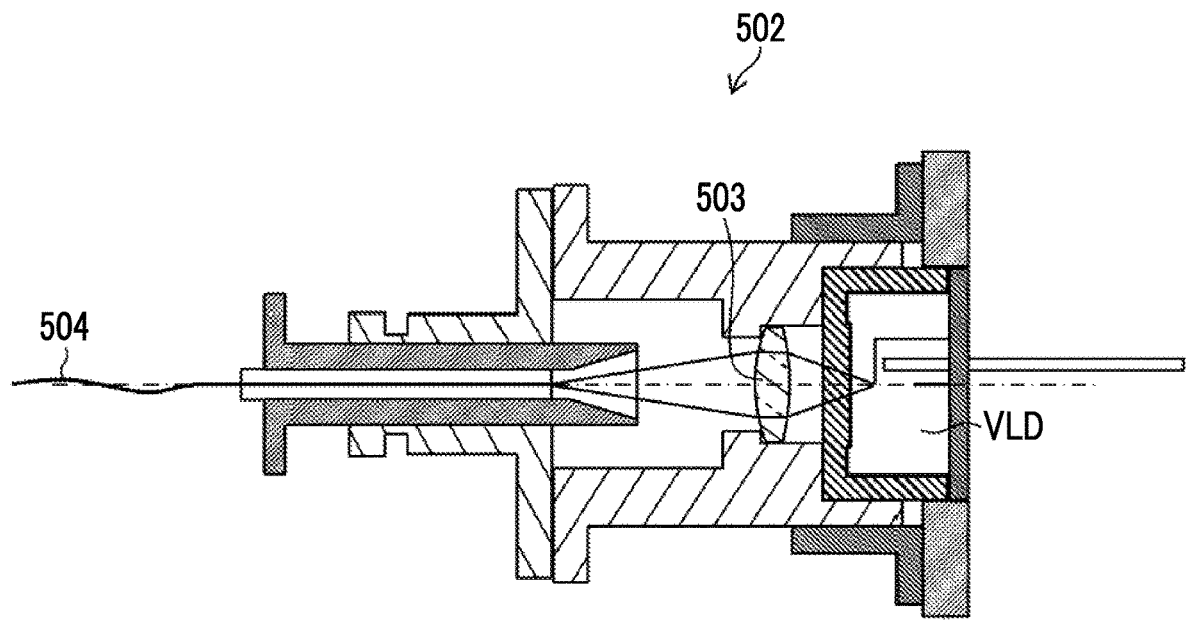
FIG. 6 is a sectional view illustrating the configuration of a laser light source module.

The laser light source module 502 is a pigtail type module (transmitter optical sub-assembly (TOSA)) including a visible laser diode (VLD) that has electrical power supplied thereto from a power source (not illustrated) and emits the laser light of a visible wavelength range, and a condensing lens 503 that condenses the laser light emitted from the VLD (refer to FIG. 6). The laser light can be emitted as necessary by the control of the endoscope processor 200 (CPU 210). By emitting the laser light only in a case where measurement is performed by radiation of spot light (measurement mode), the laser light can be used similarly to an ordinary endoscope during non-emission (normal mode). Turn-on, turn-off, and the intensity of light of the laser light source module 502 are controlled in accordance with the electrical signals from the endoscope processor 200 (a light source drive unit or a laser drive unit).

In the first embodiment, the laser light emitted by the VLD can be red laser light with a wavelength of 650 nm by a semiconductor laser. However, the wavelength of the laser light in the invention is not limited to this aspect. The laser light condensed by the condensing lens 503 is guided up to the GRIN lens 510 by the optical fiber 504. The optical fiber 504 is an optical fiber that propagates the laser light in a single transverse mode, and can form a spot with a small clear diameter, so that the size of a subject can be accurately measured. A relay connector may be provided in the middle of the optical fiber 504. In addition, in a case where the size of spot diameter or clearness does not pose a measurement problem depending on observation conditions, such as the type or size of a subject, an optical fiber that propagates the laser light in a multi-mode may be used as the optical fiber 504. Additionally as the light source, a light-emitting diode (LED) may be used instead of the semiconductor laser, or the semiconductor laser may be used in an LED light emission state below an oscillation threshold value.

The GRIN lens 510 is a cylindrical graded index type lens (radial type) of which the refractive index is at the highest thereof on the optical axis and decrease radially outward, and functions as a collimator that emits the laser light, which is guided by the optical fiber 504 and entered, as the parallel light. The spread of the beam emitted from the GRIN lens 510 can be adjusted by adjusting the length of the GRIN lens 510, and ($\lambda$/4) pitch ($\lambda$ is the wavelength of the laser light) or the like may be used to emit the laser light as the parallel beam.

The prism 512 (an optical member or a prism member) is mounted on a distal end side of the GRIN lens 510. The prism 512 is an optical member for changing the emission direction of the measurement auxiliary light. By changing the emission direction, in a case where the optical axis of the measurement auxiliary light is projected on a plane including the optical axis of the imaging optical system, the optical axis of the measurement auxiliary light has an inclination angle, which is not 0 degrees with respect to the optical axis of the imaging optical system, and the measurement auxiliary light crosses the field angle of the imaging optical system. The prism 512 is formed with a size near the lens diameter of the GRIN lens 510, and a distal end surface thereof is cut obliquely and has an apex angle AL1 (refer to an example to be described below regarding specific numerical values) according to the above-described inclination angle.

<Relationship Between Optical Axis of Imaging Optical System and Optical Axis of Measurement Auxiliary Light>

Figure 7:
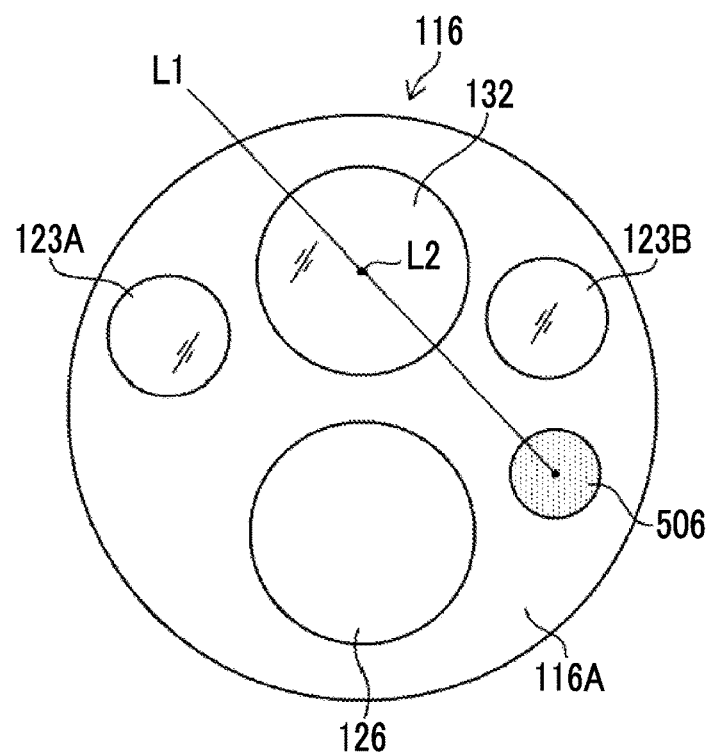
FIG. 7 is a view illustrating a relationship between an optical axis of an imaging optical system and an optical axis of measurement auxiliary light.
Figure 8:
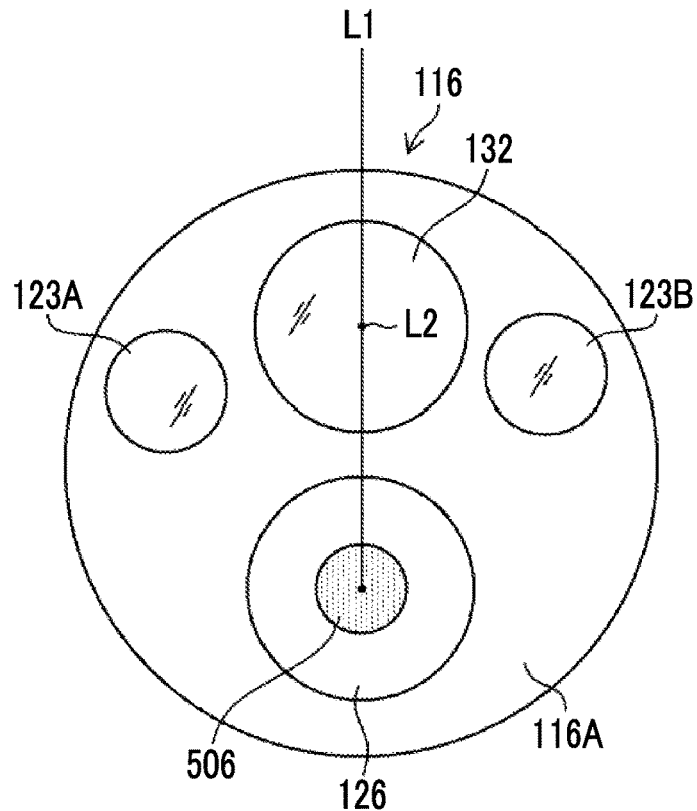
FIG. 8 is another view illustrating the relationship between the optical axis of the imaging optical system and the optical axis of the measurement auxiliary light.

FIG. 7 is a view illustrating a state where the distal end rigid part 116 related to the first embodiment is seen from the front (subject side), and is a view corresponding to the configuration of FIG. 3. In the first embodiment, an optical axis L1 of the measurement auxiliary light and an optical axis L2 of the imaging optical system are present on the same plane and intersect each other on the same plane. Hence, in a case where the distal end rigid part 116 is seen from the front (subject side), as illustrated in FIG. 7, the optical axis L2 appears to pass on the optical axis L1. In addition, FIG. 8 is a view corresponding to the configuration of FIG. 4. Also in the aspect illustrated in FIGS. 4 and 8, the optical axis L1 of the measurement auxiliary light and the optical axis L2 of the imaging optical system are present on the same plane and intersect each other on the same plane.

Figure 9:
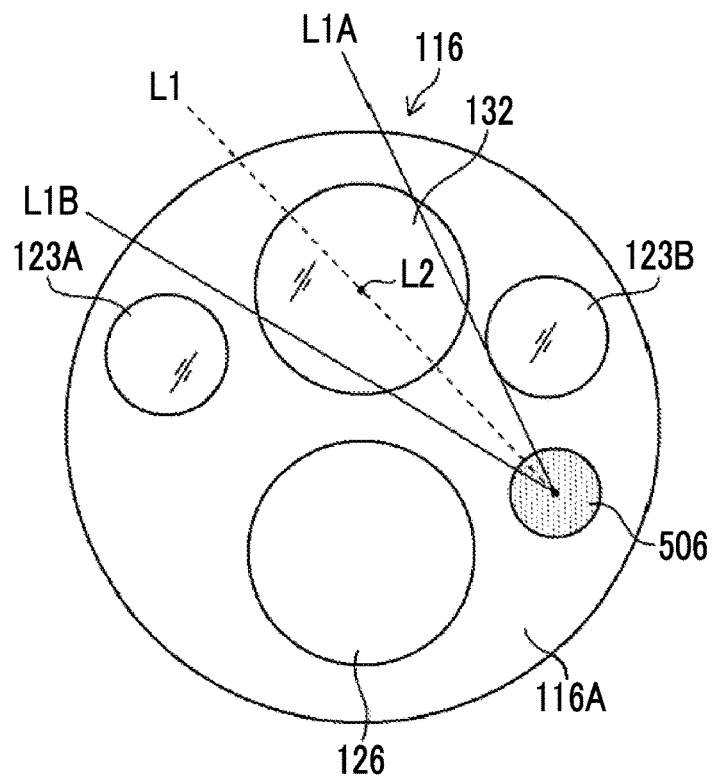
FIG. 9 is still another view illustrating the relationship between the optical axis of the imaging optical system and the optical axis of the measurement auxiliary light.

In addition, the relationship between the optical axis L1 of the measurement auxiliary light and the optical axis L2 of the imaging optical system in the invention may be limited to the above-described aspect in which "the optical axis of the measurement auxiliary light and the optical axis of the imaging optical system are present on the same plane and intersect each other on the same plane", and the optical axis of the measurement auxiliary light may not be present on the same plane as the optical axis L2 of the imaging optical system, as in optical axes L1A and L1B illustrated in FIG. 9. However, even in such a case, in a case where the optical axis of the measurement auxiliary light is projected on the plane including the optical axis of the imaging optical system, the optical axis of the measurement auxiliary light has the inclination angle, which is not 0 degrees with respect to the optical axis of the imaging optical system, and crosses the field angle of the imaging optical system.

In a case where the optical axis of the measurement auxiliary light is parallel to the optical axis of the imaging optical system (the inclination angle is 0 degrees) as in the above-described JP1996-285541A, the distance up to a point where the optical axis of the measurement auxiliary light crosses the field angle of the imaging optical system becomes long depending on the spacing between the optical axes. In that case, a spot cannot be imaged in an closest range, and the measurement is difficult. Additionally, in a case where the optical axis of the measurement auxiliary light is parallel to the optical axis of the imaging optical system, there is a case where the sensitivity of a spot position change with respect to a change in observation distance is low and sufficient measurement accuracy is not obtained. In contrast, according to the configuration in which, "in a case where the optical axis of measurement auxiliary light is projected on the plane including the optical axis of the imaging optical system, the optical axis of the measurement auxiliary light has the inclination angle, which is not 0 degrees with respect to the optical axis of the imaging optical system, and crosses the field angle of the imaging optical system" as in the first embodiment, the measurement can be made at an observation distance of a wide range from the closest range to a long range. Additionally, since the sensitivity of the spot position change with respect to the distance change is high, the measurement can be made with high accuracy.

<Configuration of Light Source Device>

As illustrated in FIG. 2, the light source device 300 is constituted of a light source 310 (illumination light source) for illumination, a stop 330, a condensing lens 340, a light source control unit 350 (control unit), and the like, and makes illumination light (the visible light or infrared light) incident on the light guide 170. The light source 310 includes a visible light source 310A (illumination light source) and an infrared light source 310B (illumination light source), and is capable of radiating one or both of the visible light and the infrared light. The illuminance of the illumination light by the visible light source 310A and the infrared light source 310B is controlled by the light source control unit 350 (control unit), and as will be described below, is adapted to be capable of lowering the illuminance of the illumination light as necessary or stopping the illumination, in a case where a spot is imaged and measured (in the measurement mode).

By coupling the light guide connector 108 (refer to FIG. 1) to the light source device 300, the illumination light radiated from the light source device 300 is transmitted to the illuminating lenses 123A and 123B via the light guide 170 and is radiated to an observation range from the illuminating lenses 123A and 123B.

<Configuration of Endoscope Processor>

Next, the configuration of the endoscope processor 200 (a measurement unit, a storage unit, a marker creation unit, a display control unit, a light source drive unit, or a laser drive unit) will be described with reference to FIG. 2. The endoscope processor 200 inputs the image signals output from the endoscope device 100 via an image input controller 202, and performs image processing required by an image processing unit 204 (the measurement unit, the marker creation unit, or the display control unit) to output the image signals via a video output unit 206. Accordingly, an observation image is displayed on the monitor 400 (display device). These kinds of processing are performed under the control of a central processing unit (CPU) 210 (the measurement unit, the marker creation unit, or the display control unit). In the image processing unit 204, switching and overlap display of images displayed on the monitor 400, electronic zooming processing, display of images according to operation modes, extraction of a specific component (for example, a luminance signal) from the image signals, and the like are performed in addition to image processing, such as white balance adjustment. Additionally, in the image processing unit 204, measurement of a spot position on the imaging surface of the imaging element 134 and calculation of the size (the number of pixels) of a marker based on the measured position are performed (to be described below).

Information required for the processing performed by the CPU 210 or the image processing unit 204, for example, a relationship between the position of a spot and the size of a marker on the imaging surface of the imaging element 134 is stored in advance in a memory 212 (storage unit). This relationship may be stored in a function form or may be stored in a look-up table form.

Additionally, the endoscope processor 200 includes the operating part 208. The operating part 208 includes an operation mode setting switch, a water supply instruction button, and the like that are not illustrated, and is capable of operating radiation of the visible light and/or the infrared light.

<Observation by Endoscope Device>

Figure 10:
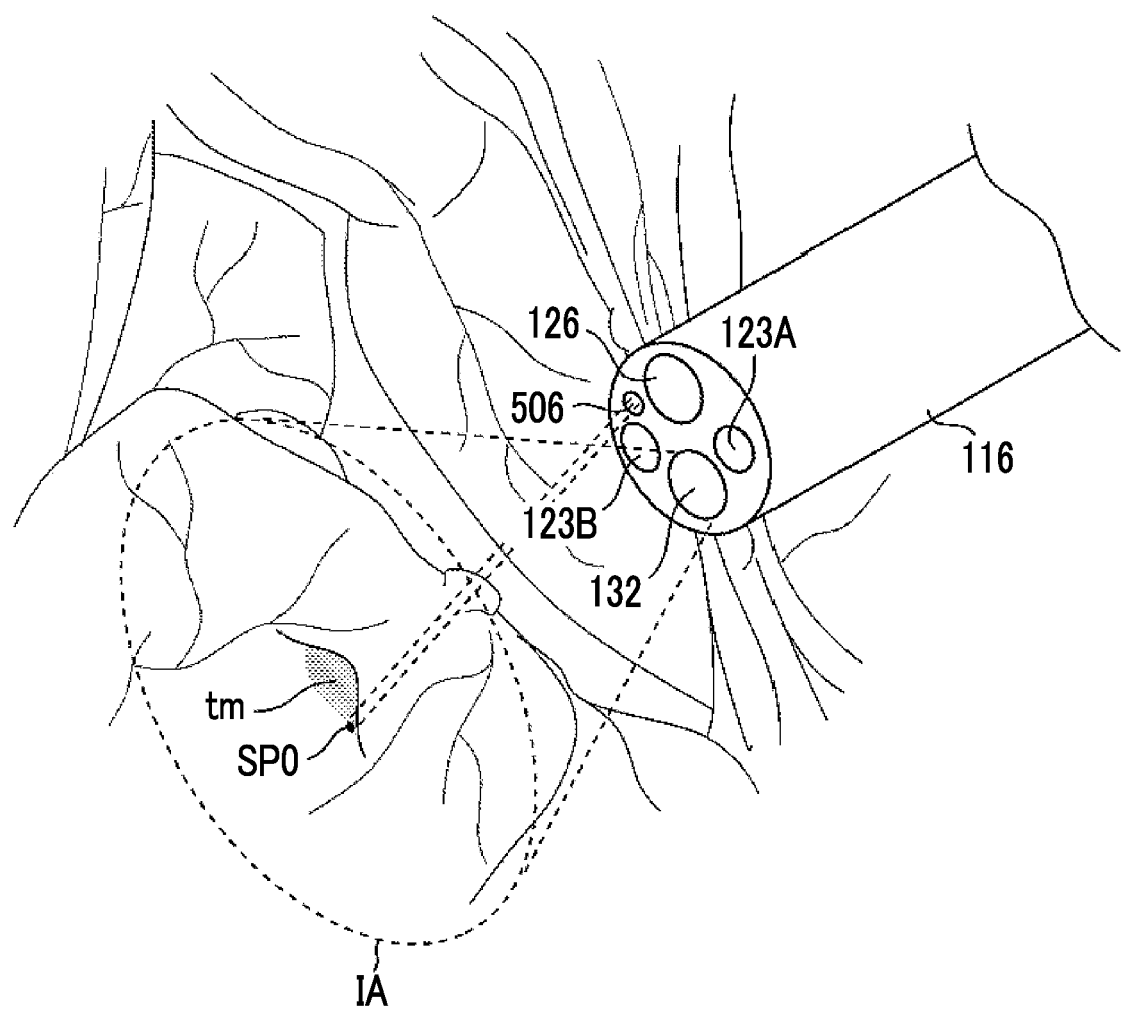
FIG. 10 is a view illustrating a state where an insertion part of an endoscope is inserted into a test object.

FIG. 10 is a view illustrating a state where the insertion part 104 of the endoscope device 100 is inserted into the test object, and illustrates a state where an observation image is acquired regarding an imaging range IA via the imaging optical system 130. FIG. 10 illustrates a state where a spot SP0 is formed in the vicinity of a tumor tm (a portion that bulges in black).

<Flow of Measuring Processing>

Figure 11:
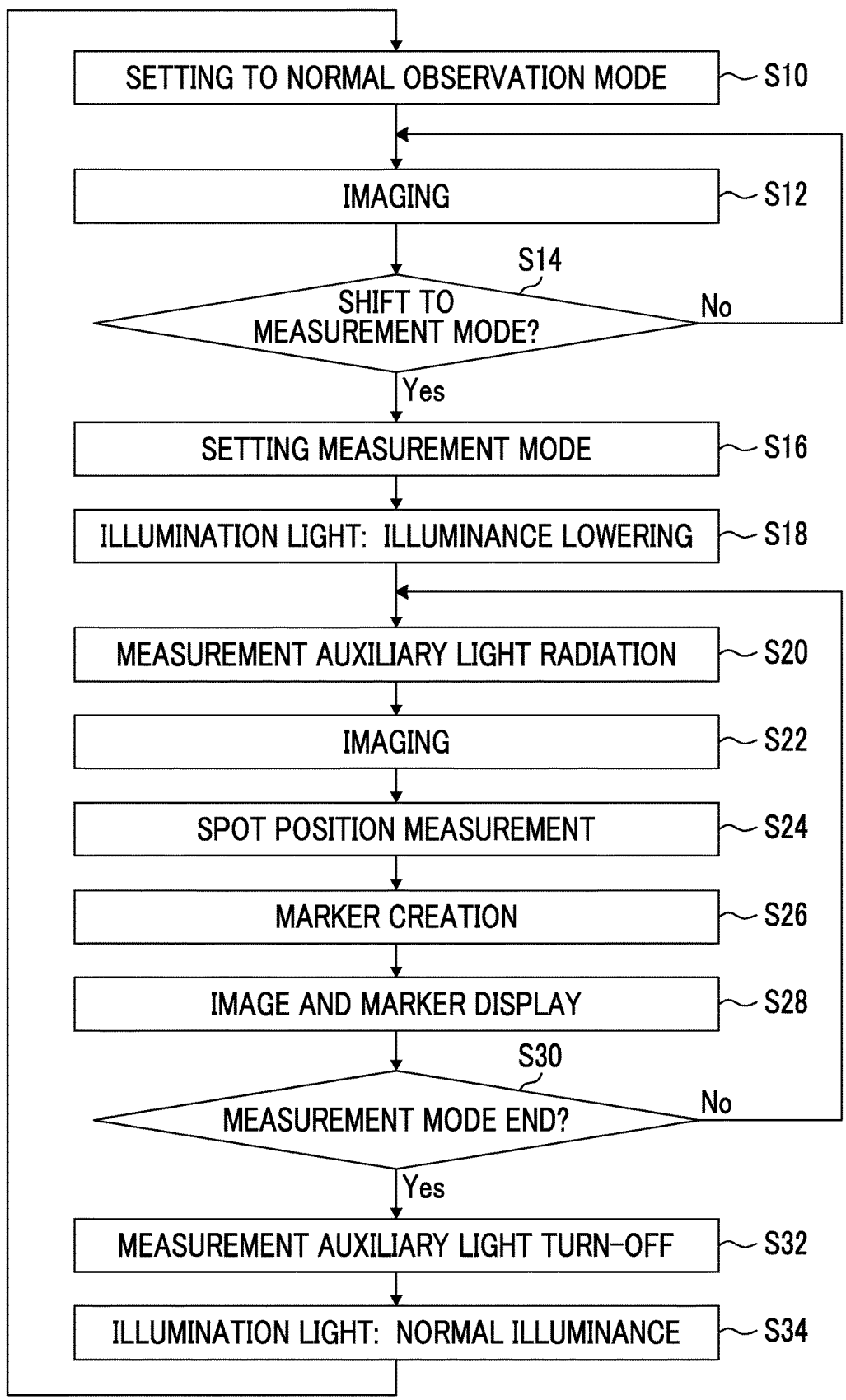
FIG. 11 is a flowchart illustrating the processing of a measurement support method.

Next, the measurement support method for the test object using the endoscope system 10 will be described. FIG. 11 is a flowchart illustrating processing of the measurement support method.

First, the insertion part 104 of the endoscope device 100 is inserted into the test object, and the endoscope system 10 is set to a normal observation mode (Step S10). The normal observation mode is a mode in which the subject is irradiated with the illumination light radiated from the light source device 300 to acquire an image and the subject is observed. The setting to the normal observation mode may be automatically performed by the endoscope processor 200 at the time of the startup of the endoscope system 10 or may be performed in accordance with the operation of the operating part 208 by a user.

In a case where the endoscope system 10 is set to the normal observation mode, the illumination light is radiated to image the subject, and the obtained image displayed on the monitor 400 (Step S12). As the image of the subject, a still image may be captured or a moving image may be captured. During the imaging, it is preferable to switch the type (the visible light or the infrared light) of the illumination light in accordance with the type of the subject or the purposes of observation. The user moves the insertion part 104 forward or backward and/or operates to bend the insertion part 104 to direct the distal end rigid part 116 to an observation target while viewing an image displayed on the monitor 400 so that the subject to be measured can be imaged.

Next, whether or not the normal observation mode shifts to a measurement mode is determined (Step S14). This determination may be performed on the basis of the presence or absence of a user's operation via the operating part 208, or may be performed on the basis of the presence or absence of a switching command from the endoscope processor 200. Additionally, the endoscope processor 200 may alternately set the normal observation mode and the measurement mode at fixed frame intervals (such as every one frame or every two frames). In a case where the determination of Step S14 is negative, the process returns to Step S12 and the imaging in the normal observation mode is continued, and in a case where the determination is positive, the process proceeds to Step S16 where switching to the measurement mode is performed.

The measurement mode is a mode in which the laser light (measurement auxiliary light) is radiated from the laser head 506 to form a spot on the subject, and a marker for measuring the size (length) of the subject on the basis of the image of the subject on which the spot is formed is created and displayed. In the first embodiment, the red laser light is used as the measurement auxiliary light. Thus, since much of a digestive tract is reddish in an endoscopic image, there is a case where the spot is not easily recognized depending on measurement conditions. Thus, in the measurement mode, the illumination light is turned off during the image acquisition and the position measurement of the spot, or the illuminance is lowered to such a degree that the recognition of the spot is not affected (Step S18), and the measurement auxiliary light is radiated from the laser head 506 (Step S20: auxiliary light emission step). Such control can be performed by the endoscope processor 200 and the light source control unit 350.

In Step S22, an image of the subject on which the spot is formed with the measurement auxiliary light is captured (imaging step). In a case where the observation distance is within a measurement range, the spot is formed within the imaging field angle of the imaging optical system 130. As will be described in detail below, the positions of spots within an image (on the imaging element) are different in accordance with the observation distance, and the sizes (the numbers of pixels) of markers to be displayed are different in accordance with the positions of the spots.

<Changes in Spot Position According to Observation Distance>

Figure 12:
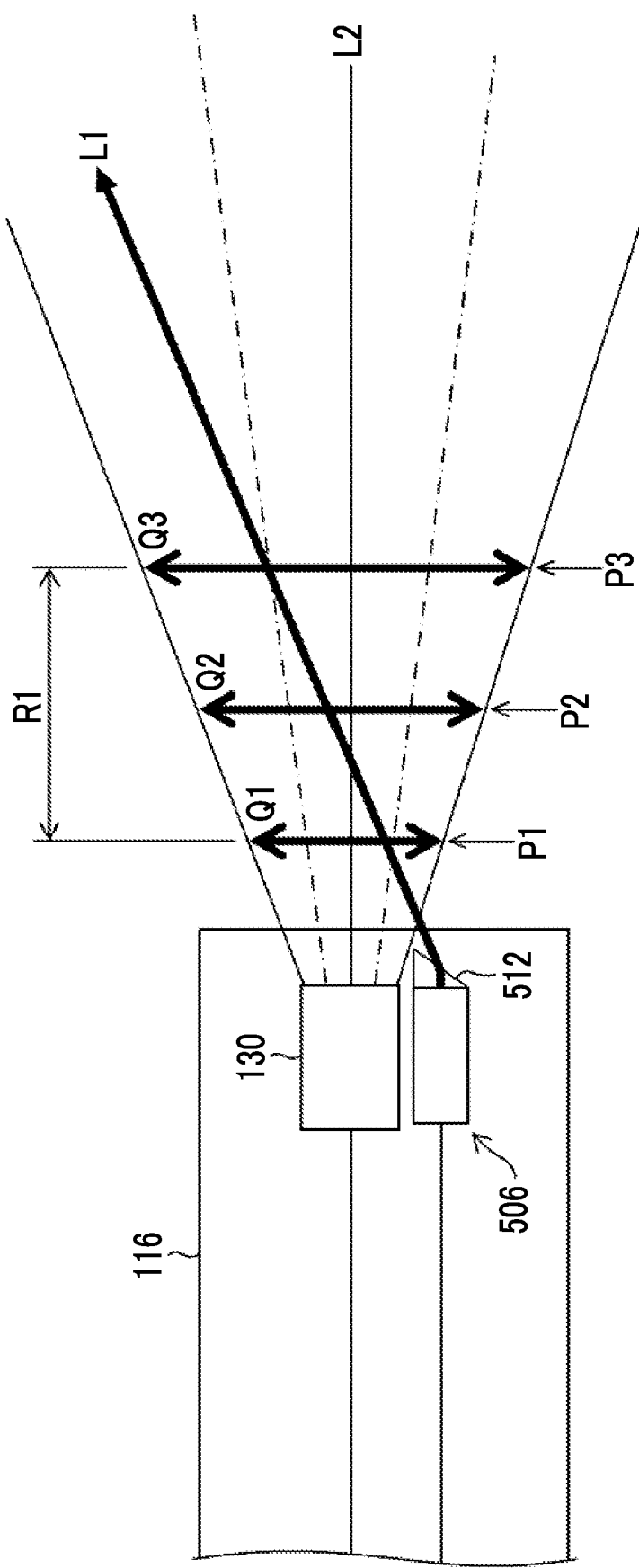
FIG. 12 is a view illustrating a state where the optical axis of the measurement auxiliary light crosses the imaging field angle of the imaging optical system.

In the first embodiment, in a case where the optical axis L1 of the measurement auxiliary light is projected on the plane including the optical axis L2 of the imaging optical system, the optical axis L1 has the inclination angle, which is not 0 degrees with respect to the optical axis L2, and crosses the field angle of the imaging optical system. Hence, the positions of spots in an image (imaging element) are different depending on distances up to subjects. For example, as illustrated in FIG. 12 (a view illustrating a state where the distal end rigid part 116 is seen from a lateral direction within the plane including the optical axis L1 and the optical axis L2), supposing that observation is possible in a range R1 of the observation distance, at a near end P1, a point P2 in the vicinity of the center, and a far end P3 in the range R1, it can be understood that the positions of spots in imaging ranges (indicated by arrows Q1, Q2, and Q3) at the respective points (points where the respective arrows and the optical axis L1 intersect each other) are different. In addition, in FIG. 12, the inside of solid lines is the imaging field angle of the imaging optical system 130, and the inside of one-dot chain lines is a measurement field angle. Measurement is performed at a central portion with small aberration among the imaging field angle of the imaging optical system 130.

Figure 13:
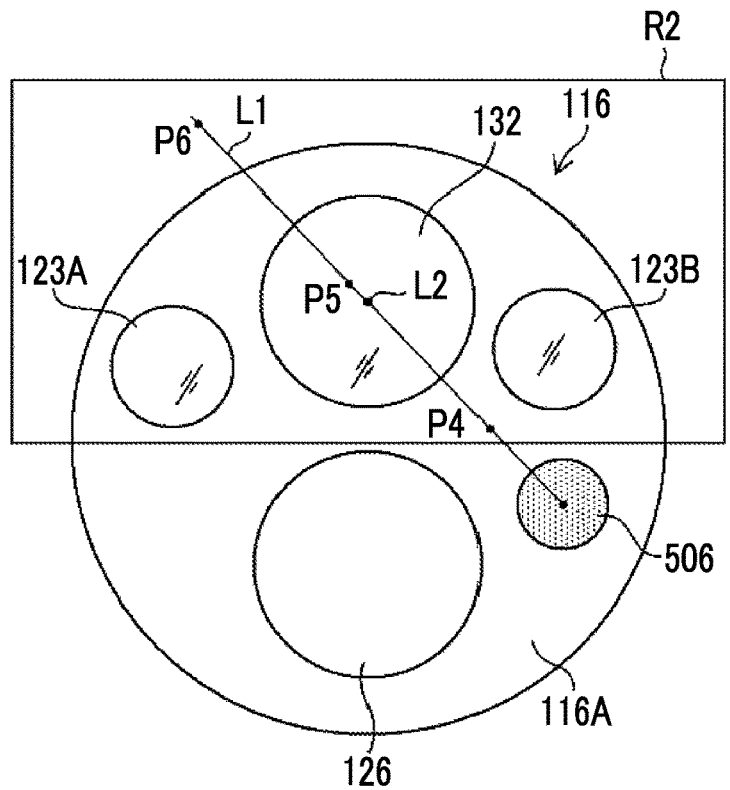
FIG. 13 is a view illustrating a state where a spot position varies depending on an imaging distance.

FIG. 13 is a view illustrating a state where the distal end rigid part 116 is seen from the front similarly to FIG. 7, and is a view virtually illustrating a relationship between the optical axis L1 of the measurement auxiliary light the optical axis L2 of the imaging optical system 130, and an imaging range R2 of the imaging element 134. FIG. 13 illustrates a case where the optical axes L1 and L2 are present on the same plane and intersect each other on the plane. In an example of FIG. 13, spot positions P4, P5, and P6 (corresponds to cases where the observation distance is in the vicinity of the near end, in the vicinity of the center, and in the vicinity of the far end, respectively) according to the observation distance are illustrated. In addition, in a case where the laser head 506 is provided in the forceps port 126 (refer to FIG. 8), as illustrated in FIG. 14, spot positions P7, P8, and P9 (correspond to cases where the observation distance is in the vicinity of the near end, in the vicinity of the center, and in the vicinity of the far end, respectively) are obtained in an imaging range R3.

Figure 14:
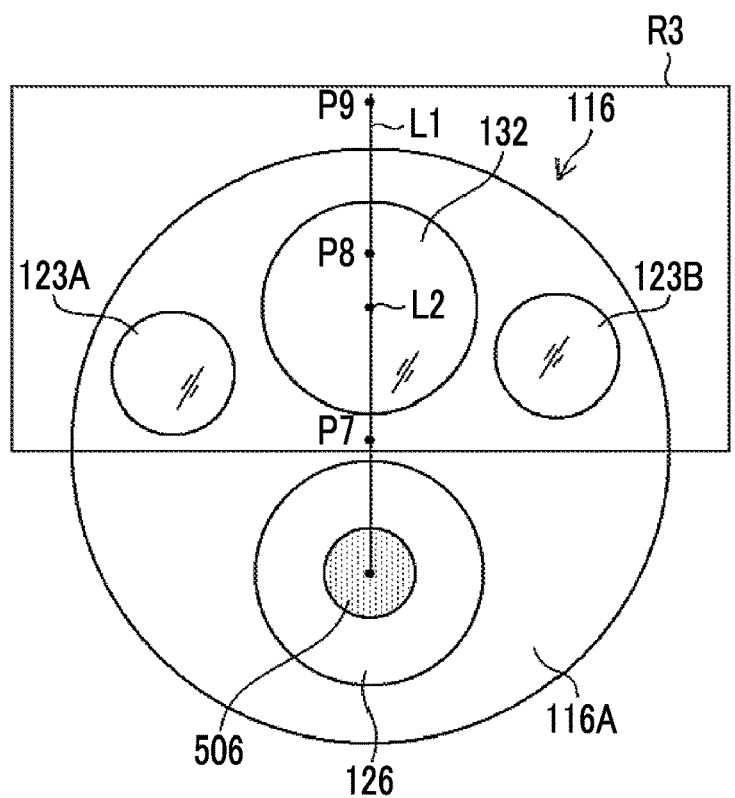
FIG. 14 is another view illustrating a state where the spot position varies depending on the imaging distance.

As illustrated in FIGS. 13 and 14, it can be understood that a spot position in a case where the observation distance is in the vicinity of the far end and a spot position in a case where the observation distance is in the vicinity of the near end are located opposite to each other with respect to the optical axis L2 of the imaging optical system 130.

Meanwhile, in the related-art technique as described in the above-described JP1996-285541A, since the optical axis of the measurement auxiliary light is parallel to the optical axis of the imaging optical system, the movement of the spot positions resulting from changes in the observation distance is small. Specifically, in a case where the observation distance is short, spots are present at positions apart from the center (the center of the imaging element) of a captured image and approach the center (the center of the imaging element) of the captured image as the observation distance becomes longer. However, the spot positions are not located on the opposite sides of the optical axis of the imaging optical system at the near end and the far end of the observation distance. In contrast to such a related-art technique, in the first embodiment, the sensitivity of the movement of the spot positions with respect to the changes in the observation distance is high as described above, and the sizes of subjects can be measured with high accuracy.

In this way, although the spot positions within the captured image (on the imaging element 134) are different in accordance with the relationship between the optical axis L2 of the imaging optical system 130 and the optical axis L1 of the measurement auxiliary light, and the observation distance. However, the number of pixels indicating the same actual size (for example, 5 mm) increases in a case where the observation distance is near, and the number of pixels decreases in a case where the observation distance is far. Hence, as will be described in detail below, the sizes of markers can be calculated by storing information indicating a relationship between the positions of spots and the sizes (the numbers of pixels) of markers corresponding to actual sizes of subjects in advance and acquiring this information according to the spot positions. In addition, it is not necessary to measure the observation distance itself at the time of calculation.

Figure 15:
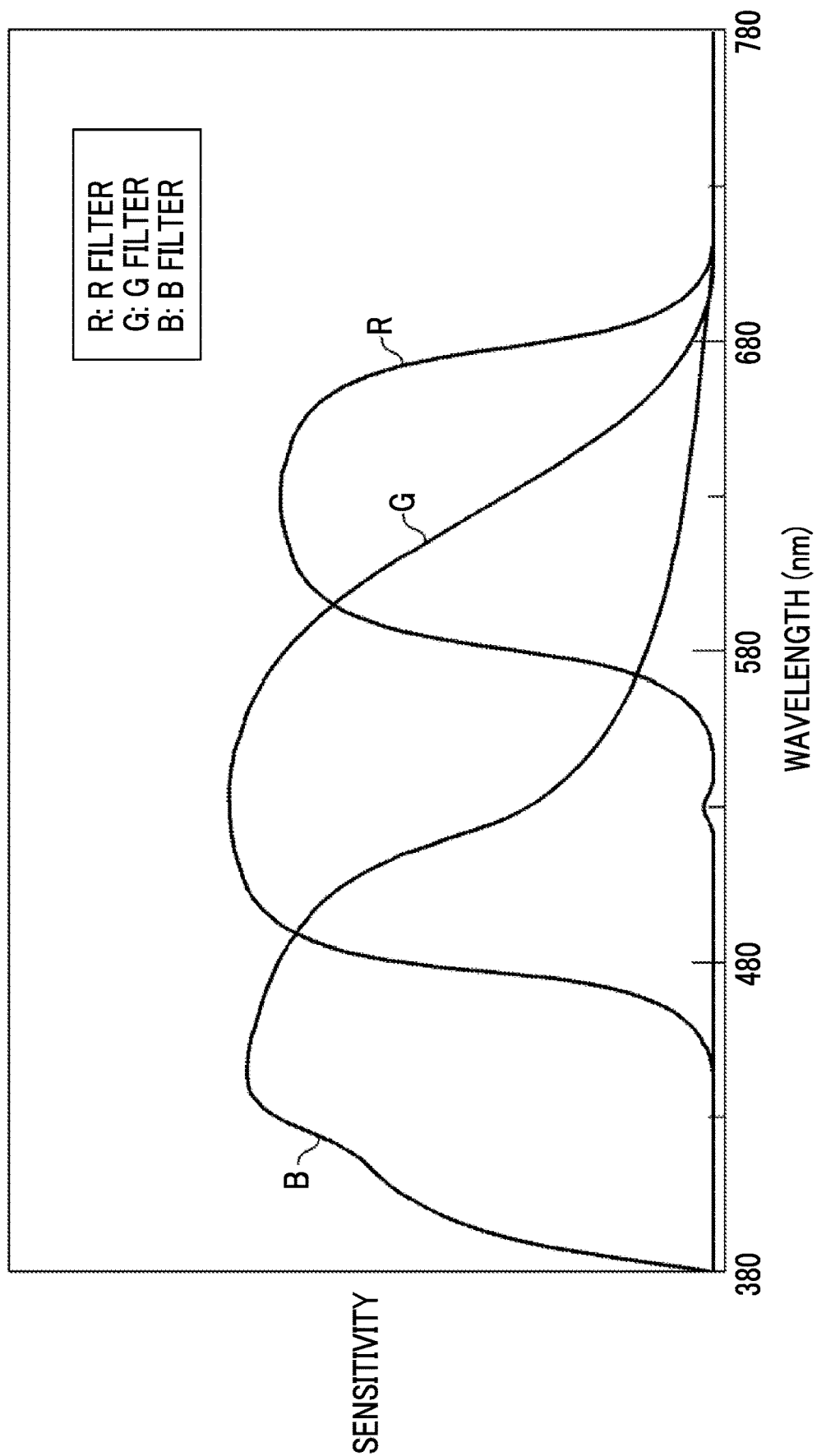
FIG. 15 is a view illustrating a relationship between wavelength and the sensitivity of color filters.

Referring to the flowchart of FIG. 11, the position measurement (Step S24: measuring step) of the spot on the imaging surface of the imaging element 134 will be described. The position measurement of the spot in Step S24 is performed by an image created by pixel signals of pixels in which color filters of a filter color of a red (R) color are disposed. Here, a relationship between the wavelength and sensitivity in color filters of respective colors (red, green, and blue) disposed in respective pixels of the imaging element 134 is as illustrated FIG. 15. Additionally, the laser light emitted from the laser head 506 is red laser light with a wavelength of 650 nm. That is, the measurement of the spot position is performed on the basis of the image created by the image signals of the pixels (R pixels) in which color filters of a red color with the highest sensitivity with respect to the wavelength of the laser light among color filters of red, green, and blue are disposed. In this case, the position of the spot can be recognized at high speed by providing a threshold value to the signal intensity of R pixels of bit map data or raw image format (RAW) data of the pixel signals to perform binarization and calculating the center of gravity of a white portion (a pixel having a higher signal intensity than the threshold value). In addition, in a case a spot is recognized by an actual image (an image created by pixel signals of all colors), it is preferable that pixel signals of pixels (G pixels and B pixels) in which green and blue color filters are disposed are provided with threshold values, and pixels in which values of the pixel signals of the G pixels and the B pixels having the bit map data are equal to or smaller than the threshold values are extracted.

In addition, the above-described technique is an example of the spot position measurement, and other well-known techniques may be adopted regarding the image recognition and the spot recognition.

In addition, in the measurement mode, as described above, the illumination light is turned off during the image acquisition (Step S22) and the position measurement (Step S24) of the spot, or the illuminance is lowered to such a degree that the recognition of the spot is not affected (Step S18), and the measurement auxiliary light is radiated from the laser head 506 (Step S20). Accordingly, an image with a clear spot can be acquired, the position of the spot can be accurately measured, and a marker of a suitable size can be created and displayed. In addition, the illumination light is not necessarily dimmed or turned off, and the illuminance remains as it is in a case where the recognition of the spot is not affected.

In Step S26, a marker indicating the actual size of the subject is created (marker creation step). As described above, since the sizes of markers are different in accordance with the positions of spots within an image (namely, on the imaging surface of the imaging element), the relationship between the positions of the spots and the sizes (the numbers of pixels) of the markers corresponding to the actual sizes of the subjects are measured in advance, information indicating the relationship is stored in the memory 212, the endoscope processor 200 acquires information from the memory 212 in accordance with the spot position measured in Step S24 and finds the size of the marker on the basis of the acquired information. A procedure of finding a relationship between spot positions and the sizes of markers will be described in detail below.

Figure 16:
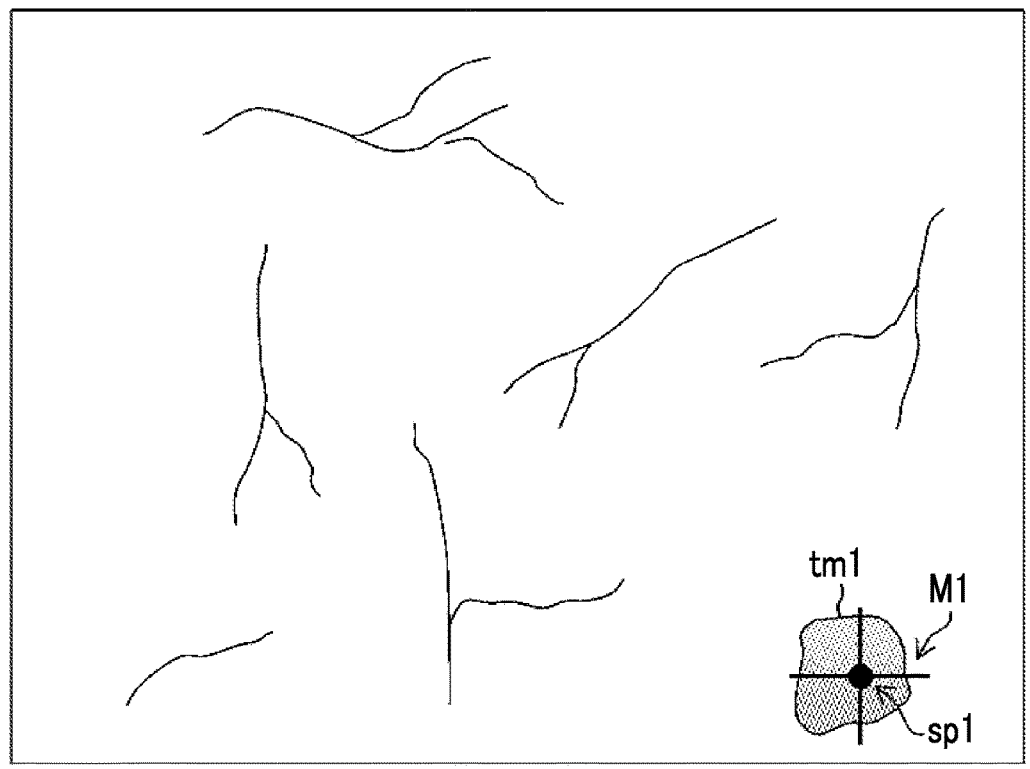
FIG. 16 is a view illustrating a state where a spot and a marker are displayed in a case where an observation distance is in the vicinity of a near end.
Figure 17:
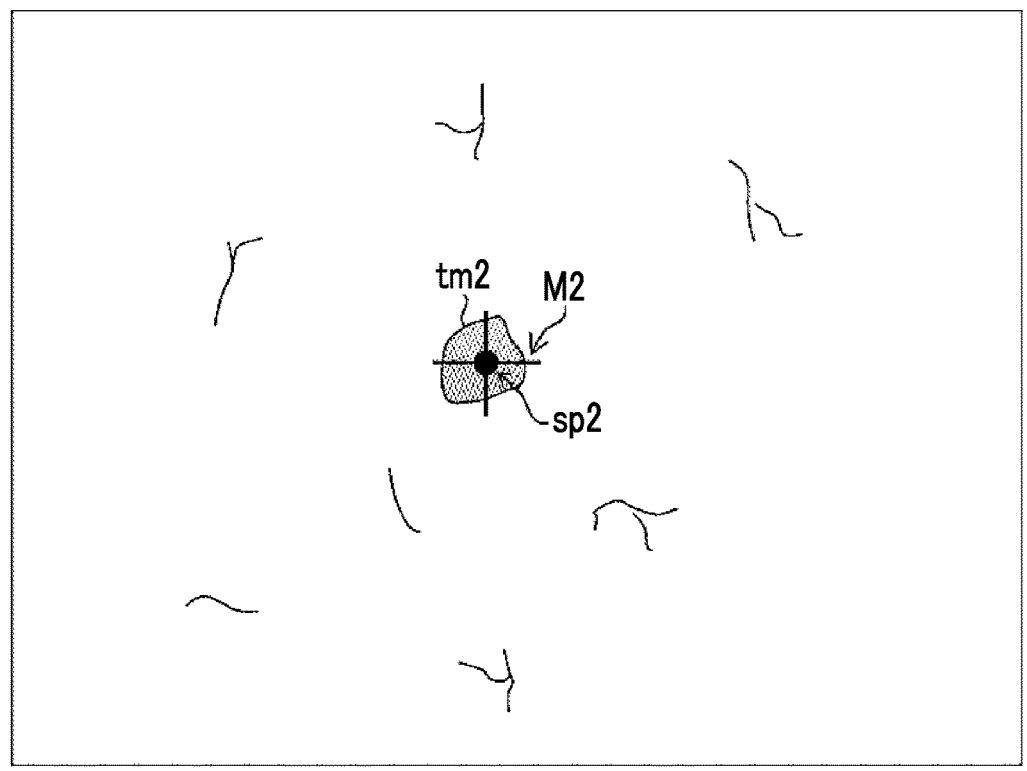
FIG. 17 is a view illustrating a state where a spot and a marker are displayed in a case where the observation distance is in the vicinity of the center of an observable range.
Figure 18:
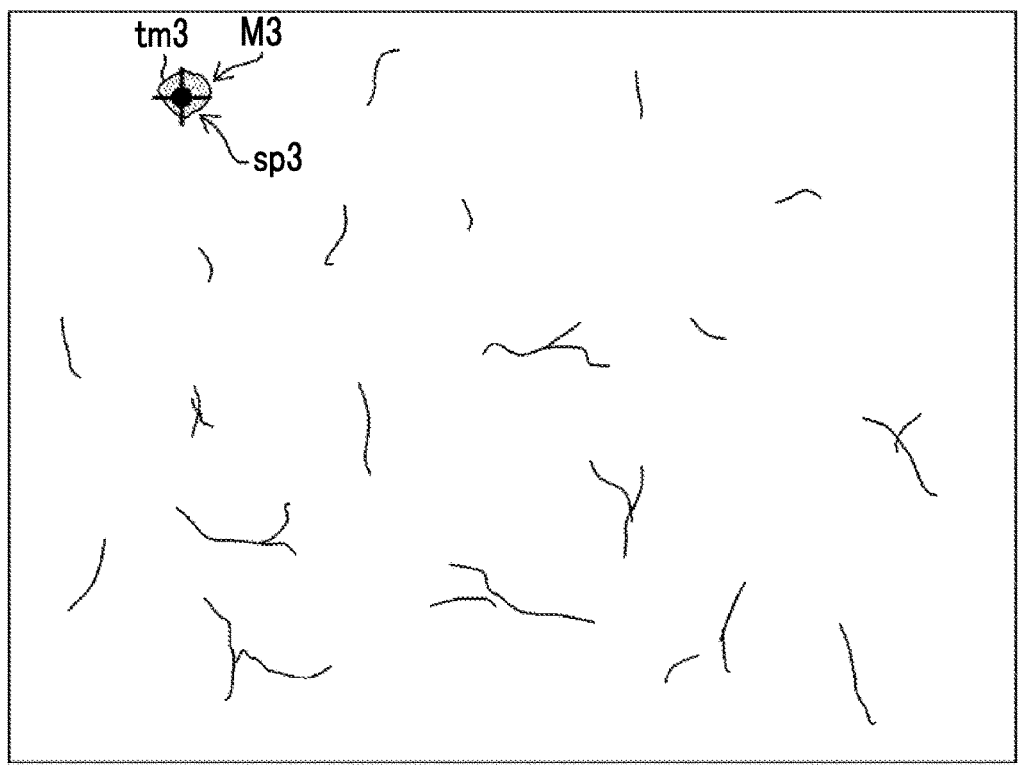
FIG. 18 is a view illustrating a state where a spot and a marker are displayed in a case where the observation distance is in the vicinity of a far end.

In Step S28, the observation image and the marker are displayed on the monitor 400 (display control step). Display conditions (the type, number, actual size, color and the like of markers) can be set by user's operation via the operating part 208. FIG. 16 is a view illustrating a state where a cross-shaped marker M1 indicating an actual size of 5 mm (a horizontal direction and a vertical direction of an observation image) is displayed in alignment with the center of a spot sp1 formed on a subject (tumor tm1) in a state where the observation distance is close to the near end. Similarly, FIG. 17 is a view illustrating a state where a marker M2 is displayed in alignment with the center of a spot sp2 (formed on a tumor tm2) in a state where the observation distance is in the vicinity of the center of the observation distance range, and FIG. 18 is a view illustrating a state where displayed a marker M3 is displayed in alignment with the center of a spot sp3 (formed on a tumor tm3) in a state where the observation distance is close to the far end. As described above, since the optical axis L1 of the measurement auxiliary light has the inclination angle that is not 0 degrees with respect to the optical axis L2 of the imaging optical system 130, the positions of spots on the imaging surface of the imaging element 134 are different depending on the observation distance. For this reason, the display positions of the markers are also different. As illustrated in FIGS. 16 to 18, the sizes of the markers with respect to the same actual size of 5 mm become smaller as the observation distance becomes longer (the numbers of pixels of the markers decrease).

Figure 19:
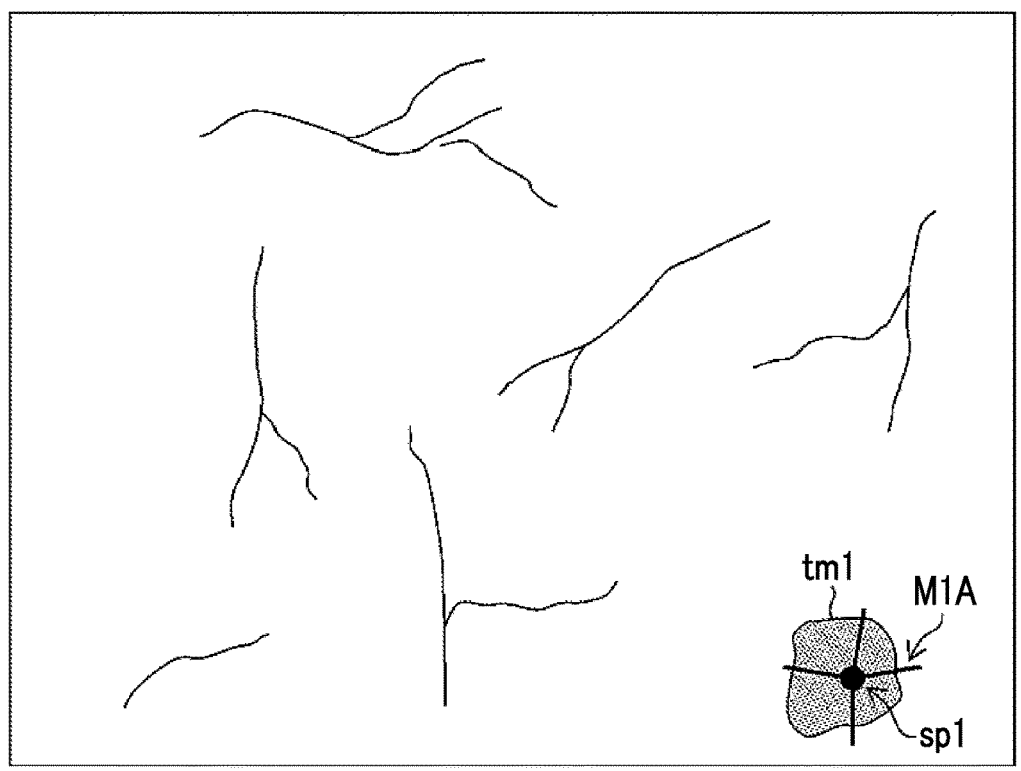
FIG. 19 is a view illustrating a state where the spot and a deformed marker are displayed in a case where the observation distance is in the vicinity of the near end.
Figure 20:
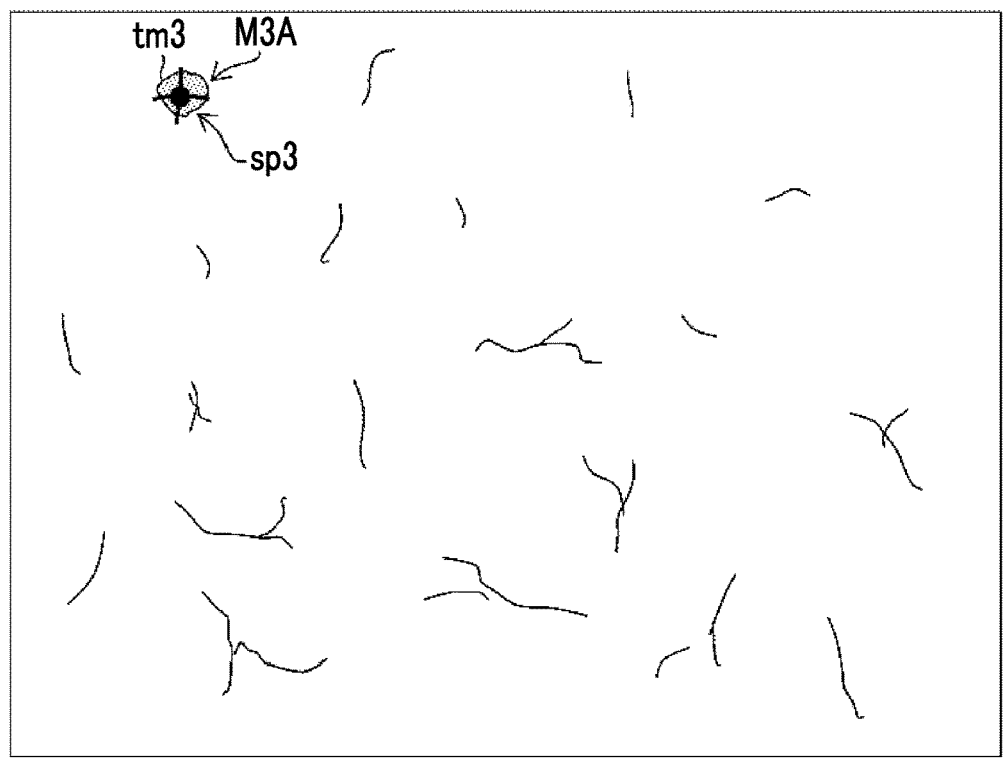
FIG. 20 is a view illustrating a state where the spot and a deformed marker are displayed in a case where the observation distance is in the vicinity of the far end.

In the above-described FIGS. 16 to 18, the influence of the distortion aberration of the imaging optical system 130 is not taken into consideration. However, generally, optical systems used for endoscopes have wide angle and large distortion aberration, and there is also influence on the shapes of subjects in a captured image. Hence, it is preferable that the markers are also displayed in forms in which the influence of the distortion aberration are taken into consideration (corrected). In this case, since the distortion aberration is little at a central portion of an optical system and is large at a peripheral portion, the presence or absence of the correction may be determined in accordance with the display positions (spot positions) of the markers. FIGS. 19 and 20 are examples in which markers M1 and M3 are deformed and displayed as markers M1A and M3A at peripheral portions with large distortion aberration. In this way, by displaying the markers, the sizes of the subjects can be accurately measured. In addition, data of the distortion aberration may be set on the basis of the design values of the imaging optical system 130 or may be separately measured and acquired.

In addition, in FIGS. 16 to 18, the center of a spot and the center of a marker are displayed so as to coincide with each other. However, in a case where there is no measurement accuracy problem, a marker may be displayed at a position apart from a spot. However, even in this case, it is preferable to display the marker in the vicinity of the spot.

In addition, instead of the deforming and displaying a marker, the distortion aberration of a captured image may be corrected, and a marker that is not deformed may be displayed on the image after the correction.

In addition, in FIGS. 16 to 20, the markers corresponding to the actual size of 5 mm of the subjects are displayed. However, the actual size of subjects may be set to any values (for example, 2 mm, 3 mm, 10 mm, and the like) in accordance to observation targets or observation purposes. Additionally, although the cross-shaped markers are displayed in FIGS. 16 to 20, markers of a circular shape and other shapes may be displayed. The number of markers may be one or plural, or the color of markers may be changed in accordance with the actual sizes. Such display modes may be selected by operation via the operating part 208.

By contrasting such markers with the subjects, the user can easily measure the sizes (about 5 mm in both the horizontal direction and the vertical direction in the examples of FIGS. 16 to 20) of the subjects without measuring the observation distance.

In Step S30, whether or not the measurement mode is ended is determined. This determination may be performed on the basis of a user's operation via the operating part 208, or may be performed on the basis of a switching command from the endoscope processor 200. Additionally, similarly to during the shift to the measurement mode, in a case where a certain number of frames have elapsed, the measurement mode may be automatically ended and may return to the normal observation mode. In a case where the determination of Step S30 is negative, the process returns to Step S20 and the processing of Step S20 to Step S28 is repeated. In a case where the determination of Step S30 is positive, the process proceeds to Step S32 where the measurement auxiliary light is turned off, subsequently the illuminance of the illumination light is returned to normal illuminance in Step S34, and the process returns to the normal observation mode (returns to Step S10). In addition, in a case where there is no hindrance in the observation in the normal observation mode, the measurement auxiliary light may not be turned off.

Figure 34:
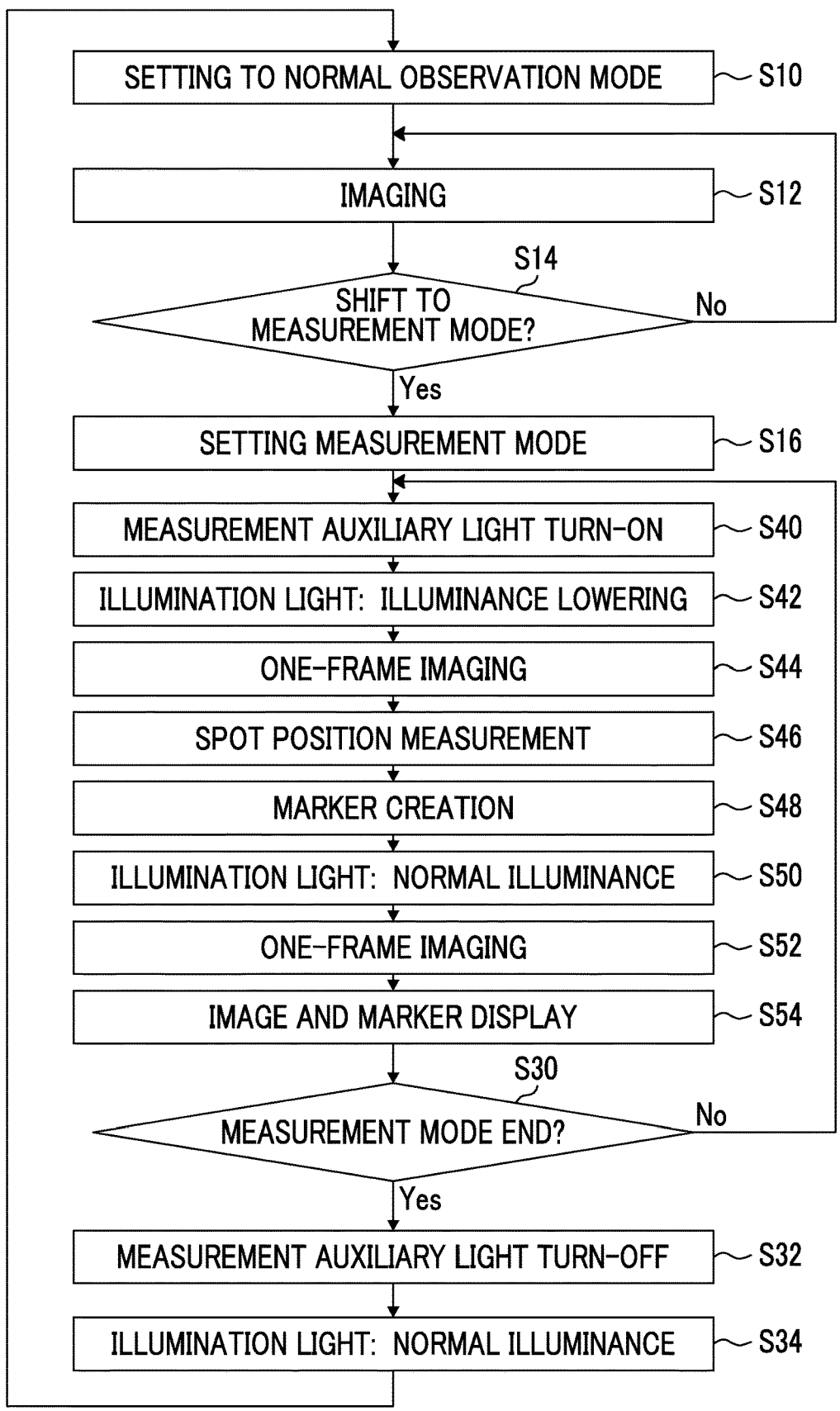
FIG. 34 is another flowchart illustrating the processing of the measurement support method.

In the above-described method, in a case where an image obtained in the measurement mode becomes dark and diagnosis becomes difficult, measurement may be performed in accordance with a procedure illustrated in a flowchart of FIG. 34. In a flowchart of FIG. 34, in one frame after measurement auxiliary light turn-on (Step S40), illumination for measurement is made dark (Step S42) and imaged (Step S44), and measurement (Step S46) of a spot position and marker creation (Step S48) are performed on the basis of a captured image. In the subsequent one frame, normal illumination light quantity is set (Step S52) and captured (Step S50). In the diagnosis and the observation using the measurement auxiliary light, by creating (Step S48) marker information from the dark image (the image captured in Step S44), and overlapping displaying (Step S54) this captured image on the image (the image captured in Step S52) of the normal illumination light quantity, the brightness of an observation image can be made the same as that in the case of normal illumination. In addition, in the flowchart of FIG. 34, the same portions as those of the flowchart of FIG. 11 will be designated by the same step numbers and the description thereof will be omitted.

As described above, according to the endoscope system 10 (the measurement support device, the endoscope system, and the processor for an endoscope system) related to the first embodiment, and the measurement support method using this, the sizes of subjects can be easily and highly accurately measured.

<Measurement of Relationship Between Spot Position and Size of Marker>

In the first embodiment, the relationship between the positions of the spots on the imaging surface of the imaging element 134 and the sizes (the numbers of pixels) of the markers corresponding to the actual sizes of the subjects are measured in advance, and is stored in the memory 212 in association with the spot positions, and the size of a marker is calculated with reference to this relationship in accordance with a measured spot position. Hereinafter, an example of a measurement procedure of the relationship between spot positions and the sizes of markers will be described. In addition, here, although the markers are cross-shaped and an actual size in the horizontal direction and in the vertical direction is described as 5 mm, the markers in the invention are not limited to such an aspect.

The relationship between the spot positions and the sizes of the markers can be obtained by imaging a chart on which patterns of the actual size are regularly formed. For example, a spot is fondled by emitting the measurement auxiliary light, a grid-sheet-like chart of the same ruled lines (5 mm ruled lines) as the actual size or ruled lines (for example, 1 mm ruled lines) finer than the actual size is imaged while changing the observation distance to change the position of the spot, and a relationship between a spot position (pixel coordinates on the imaging surface of the imaging element) and the number of pixels corresponding to the actual size (how many pixels the actual size of 5 mm is represented) is acquired.

Figure 21:
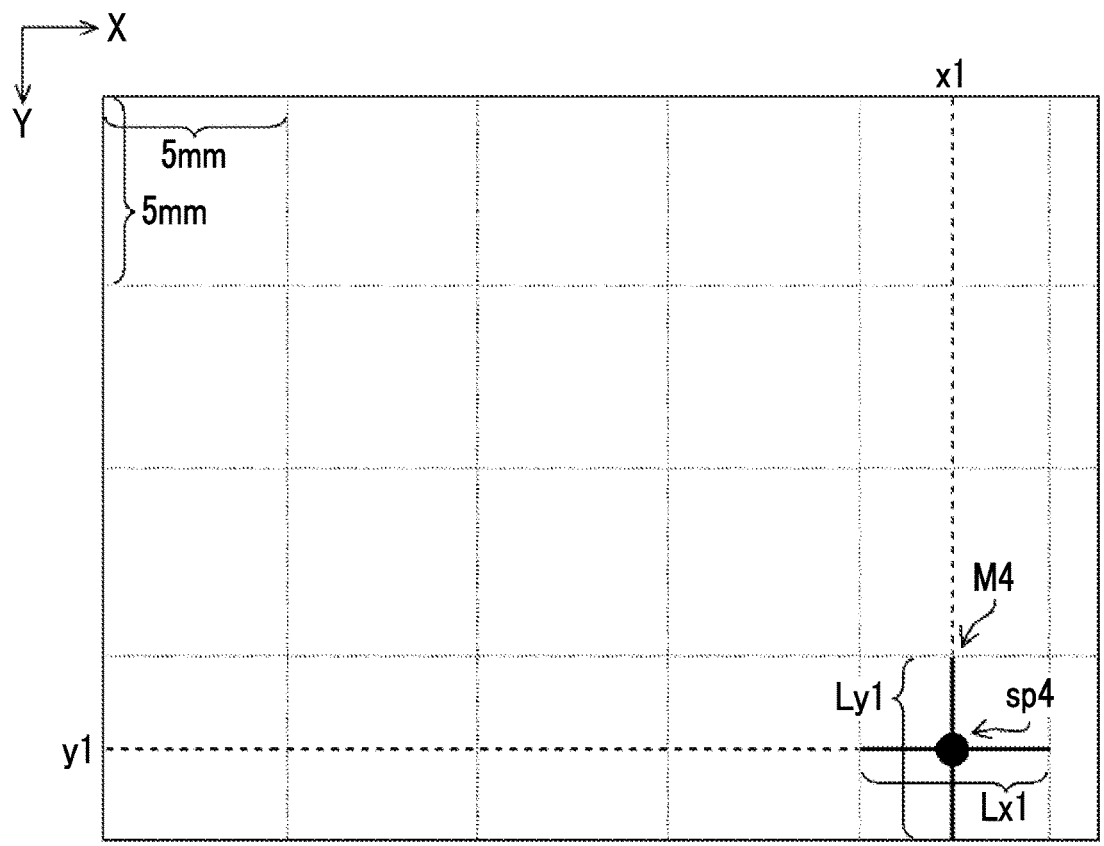
FIG. 21 is a view illustrating a state where a relationship between a spot position and the size of a marker is measured.
Figure 22:
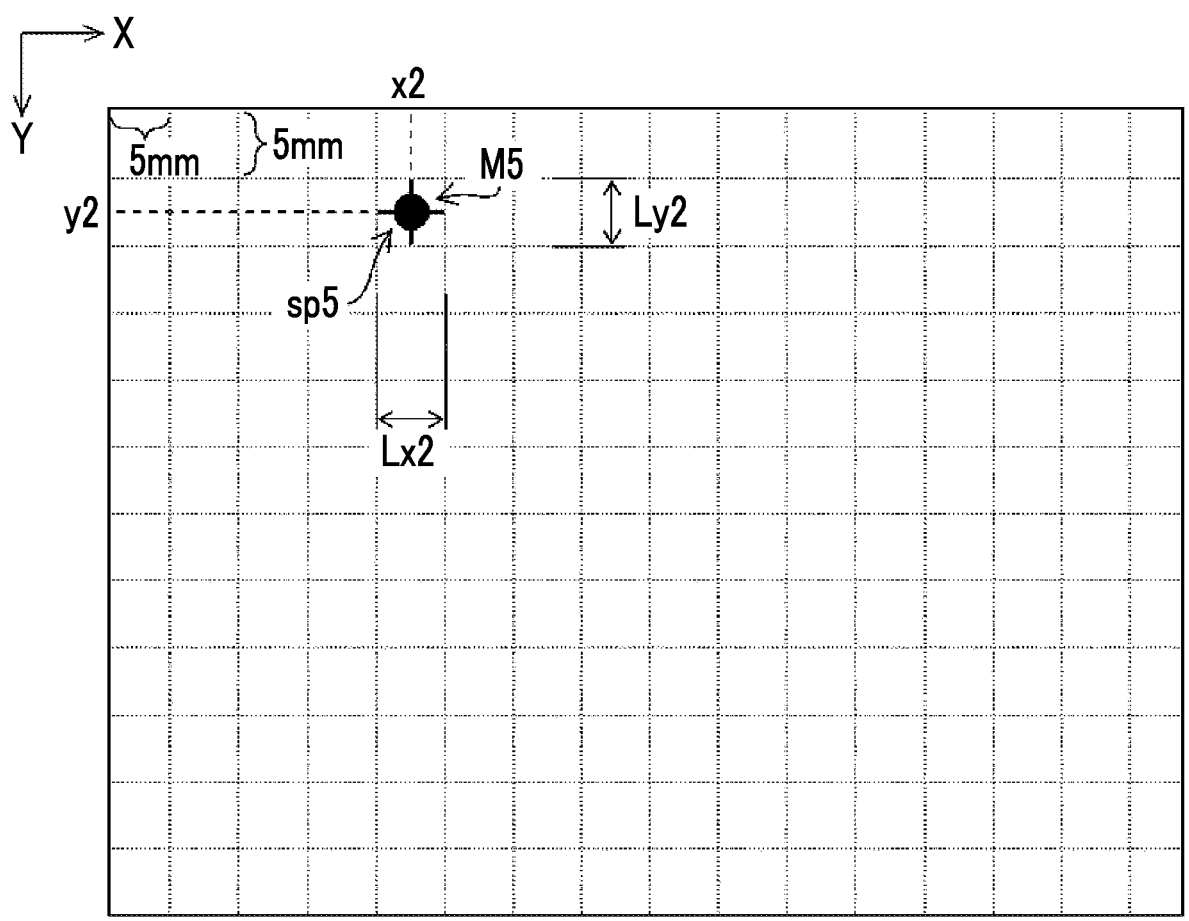
FIG. 22 is a view illustrating another state where a relationship between a spot position and the size of a marker is measured.

FIG. 21 is a view illustrating a state where the chart of the 5 mm ruled lines is imaged. The imaging distance is in a state close to the near end, and the intervals of the ruled lines are wide. In FIG. 21, (x1, y1) is an X-, Y-direction pixel position (the upper left of FIG. 21 is an origin of a coordinate system) of a spot sp4 on the imaging surface of the imaging element 134. The number of X-direction pixels, corresponding to the actual size of 5 mm, at the position (x1, y1) of the spot sp4 is set to Lx1, and the number of Y-direction pixels is set to Ly1. Such measurement is repeated while changing the observation distance. Although FIG. 22 is a view illustrating a state where a chart of the same 5 mm ruled lines as those in FIG. 21 is imaged, the imaging distance is in a state closer to the far end than the state of FIG. 21, and the intervals of the ruled lines are narrow. In the state of FIG. 22, the number of X-direction pixels, corresponding to the actual size of 5 mm, at a position (x2, y2) of a spot sp5 on the imaging surface of the imaging element 134 is set to Lx2, and the number of Y-direction pixels is set to Ly2. The measurement as illustrated in FIGS. 21 and 22 is repeated while changing the observation distance, and results are plotted. In addition, in FIGS. 21 and 22, display is performed regardless of the distortion aberration of the imaging optical system 130.

Figure 23:
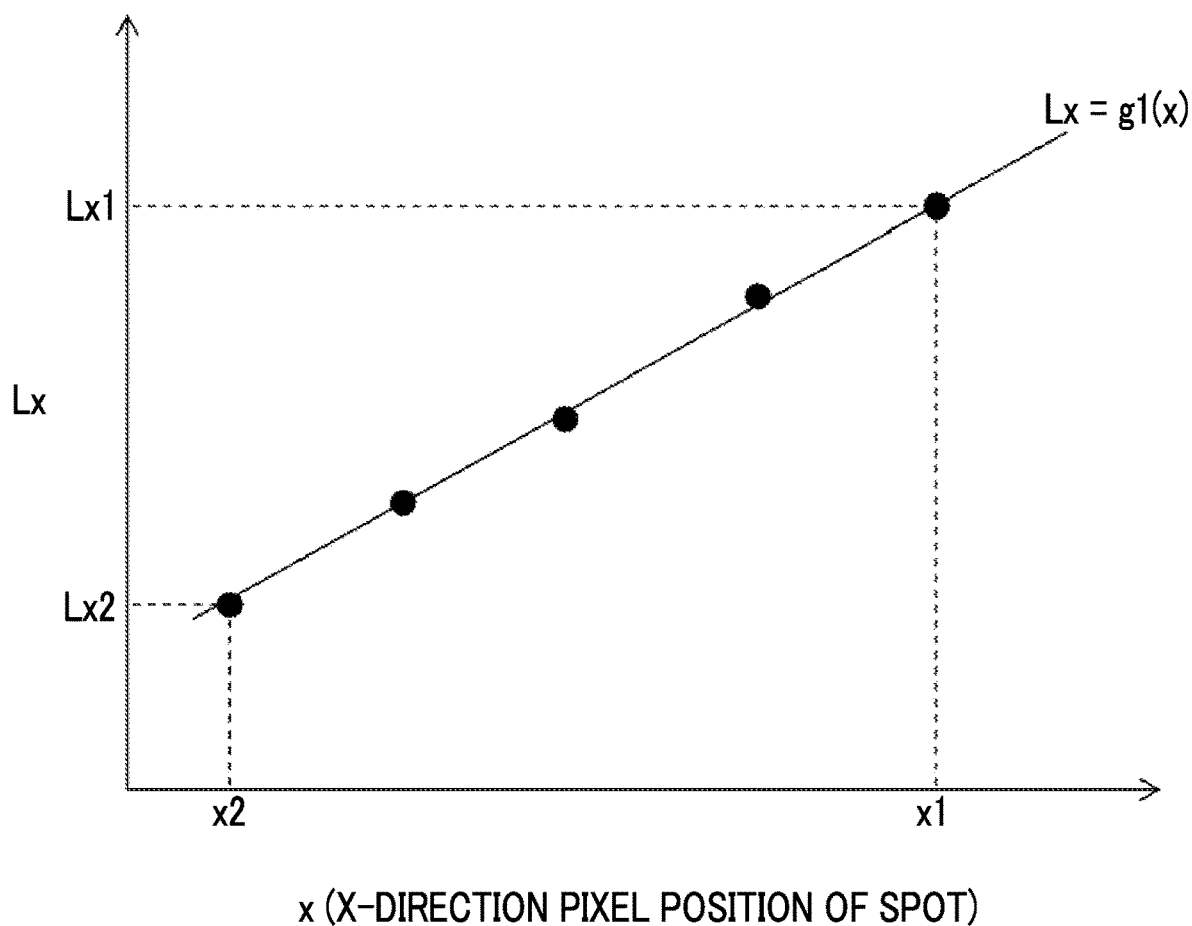
FIG. 23 is a view illustrating a relationship between the X-direction pixel positions of spots and the numbers of pixels of markers in the X-axis direction.
Figure 24:
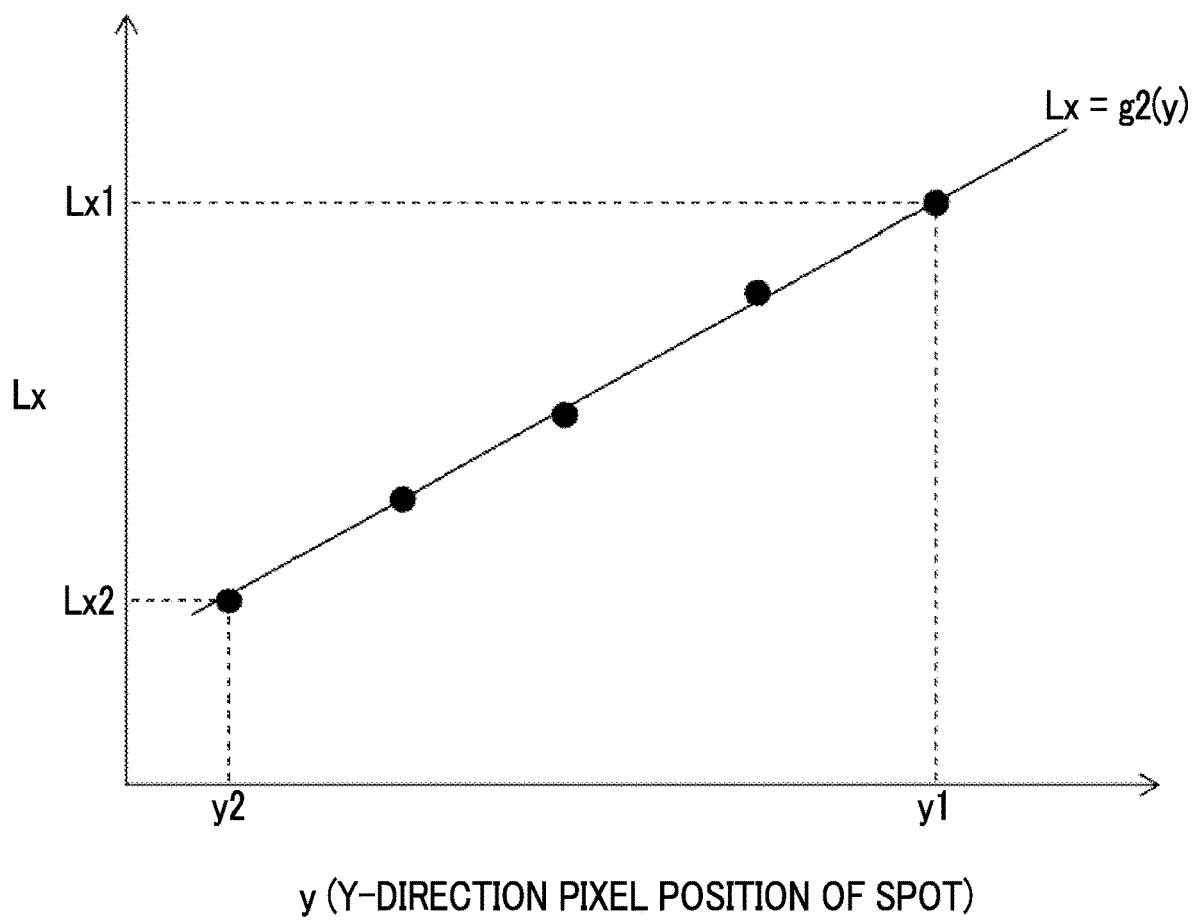
FIG. 24 is a view illustrating a relationship between the Y-direction pixel positions of spots and the numbers of pixels of markers in the X-axis direction.

FIG. 23 is a view illustrating a relationship between X coordinates of spot positions and Lx (the numbers of X-direction pixels of markers), and FIG. 24 is a view illustrating a relationship between Y coordinates of spot positions, and Lx. L(x) is expressed as Lx=g1(x) as a function of X-direction positions from the relationship of FIG. 23, and is expressed as Lx=g2(y) as a function of Y-direction positions from the relationship of FIG. 24. g1 and g2 can be found by, for example, the least-square method from the above-described plot results. In this way, the two functions g1 and g2 indicating Lx are obtained. However, the X coordinates and the Y coordinates of the spots have a one to one correspondence, and basically the same results (the same numbers of pixels for the same spot positions) are obtained even in a case where either g1 or g2 is used. Therefore, any function may be used in a case where the sizes of the markers are calculated. A function with a higher sensitivity of pixel number changes with respect to position changes may be chosen out of g1 and g2. Additionally, in a case where the values of g1 and g2 are greatly different, it may be determined that "A spot could not be recognized."

In the first embodiment, information indicating the functions g1 and g2 obtained in this way is stored in advance in the memory 212 depending on function forms, look-up table forms, and the like.

Figure 25:
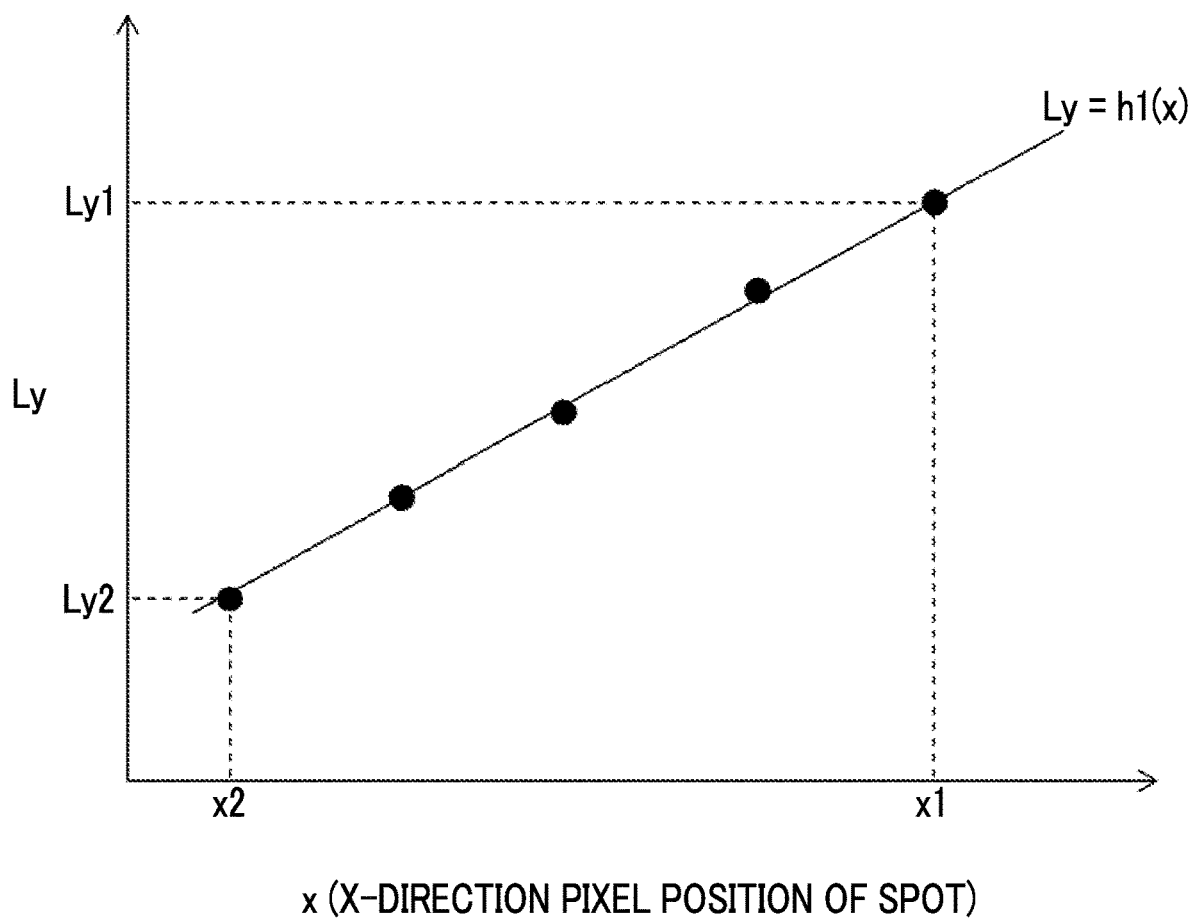
FIG. 25 is a view illustrating a relationship between the X-direction pixel positions of the spots and the numbers of pixels of the markers in the Y-axis direction.
Figure 26:
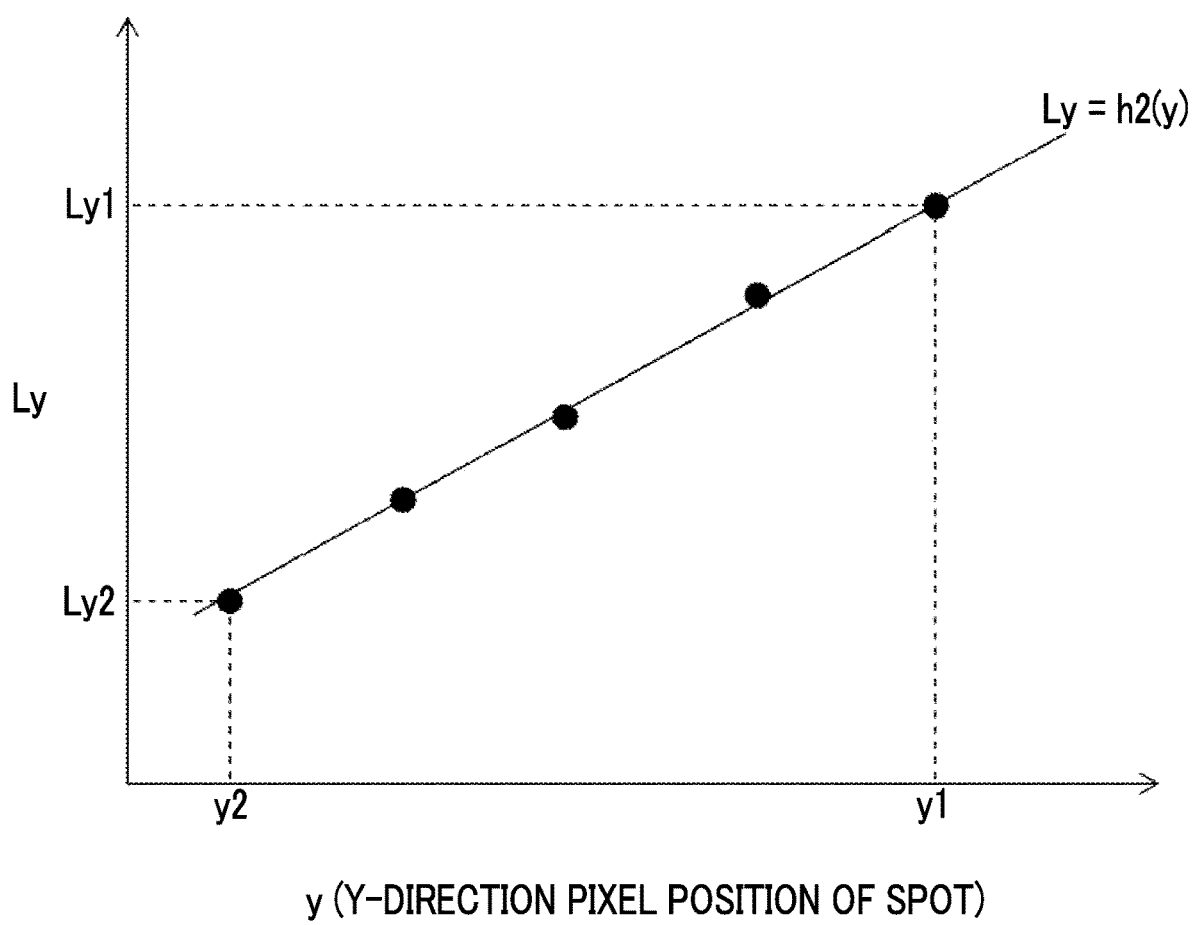
FIG. 26 is a view illustrating a relationship between the Y-direction pixel positions of the spots and the numbers of pixels of the markers in the Y-axis direction.

Additionally, FIG. 25 is a view illustrating a relationship between X coordinates of spot positions and Ly (the numbers of Y-direction pixels of the markers), and FIG. 26 is a view illustrating a relationship between Y coordinates of the spot positions, and Ly. L(y) is expressed as Ly=h1(x) as a function of the X-direction positions from the relationship of FIG. 25, and is expressed as Ly=h2(y) as a function of the Y-direction positions from the relationship of FIG. 26. Regarding Ly, similarly to Lx, any of the function h1 and h2 may be used.

Example and Comparative Example

Next, preferable values of the inclination angle of the measurement auxiliary light will be described using an example and a comparative example.

<Definition of Parameter>

Figure 27:
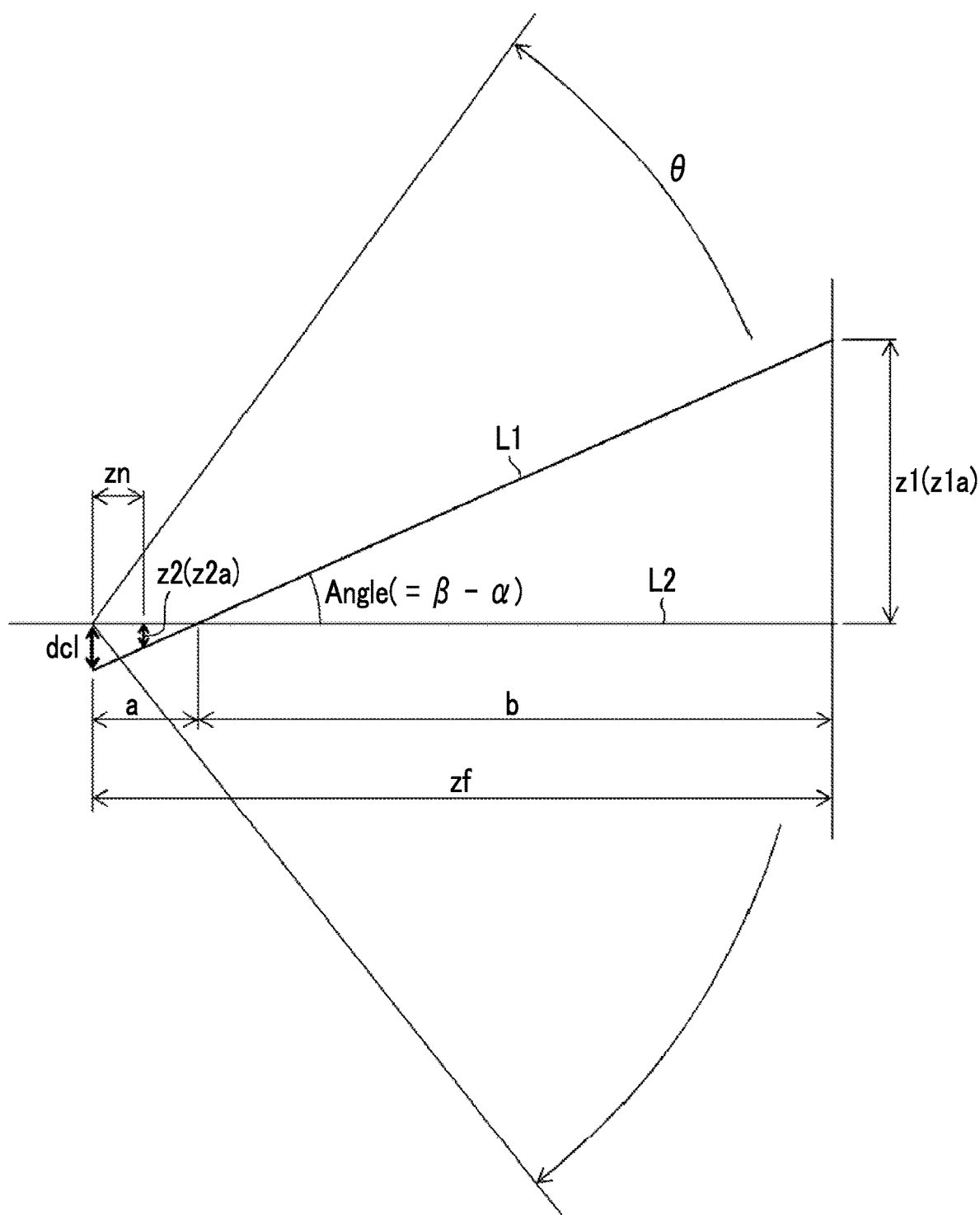
FIG. 27 is a view illustrating the definition of parameters in an example of the invention.

The definition of parameters to be used in the embodiment and the comparative example will be described referring to FIGS. 27 and 28. It is considered that a positional relationship between the laser head 506 and the imaging optical system 130 is projected on a two-dimensional plane including the optical axis L2 of the imaging optical system 130. A measurement (length measurement) range is defined as a distance from the distal end of the imaging optical system 130, the near end is zn (mm), and the far end is zf (mm). A center-to-center distance between the laser head 506 and the imaging optical system 130 is dcl (mm). The field angle that can be observed by the imaging optical system 130 is θ (degree; deg). As for the position of a spot at the far end, the distance of the position from the optical axis L2 of the imaging optical system 130 is z1 (mm). Additionally, the image height of the position in that case is z1a. As for the position of a spot at the near end, the distance of the position from the optical axis L2 of the imaging optical system 130 is z2 (mm). Additionally, the image height of the position in that case is z2a. As for a position where the laser light (measurement auxiliary light) crosses the optical axis L2 of the imaging optical system 130, the distance of the position from the distal end of the imaging optical system 130 is a (mm), and a distance from the crossing position to the far end is b (mm). In addition, since a positional relationship between the laser head 506 and the imaging optical system 130 is projected on the above-described two-dimensional plane in FIG. 27, both the optical axes do not necessarily intersect each other in a three-dimensional space (both the optical axes may have a relationship as illustrated in FIGS. 7 and 8 or may have a relationship as illustrated in FIG. 9). An angle (the inclination angle of the measurement auxiliary light) formed between the optical axis L2 of the imaging optical system 130 and the optical axis L1 of the measurement auxiliary light is Angle (degree). In a case where the refractive index of the prism 512 is n, an apex angle (refer to FIG. 28) of the prism 512 is α (degree) (the apex angle α corresponds to the apex angle AL1 of FIG. 5). Additionally, as illustrated in FIG. 28, an angle at which the emission direction of the measurement auxiliary light is formed with a line perpendicular to a mirror plane 512A of the prism 512 is β (degree). In FIG. 28, portion (a), portion (b), and portion (c) are respectively a side view, a top view, and a back view of the prism 512. In addition, although either an optical glass having a common name of "BK7" (titanium oxide) or TiO2 is used as a material ("Material" of FIG. 29) of the prism 512 (are different depending on examples and a comparative example; refer to FIG. 29), the invention is not limited to this, and glass materials or the like used for lenses may be used.

In images of endoscopes, generally, the distortion aberration is large and the length measurement at a peripheral portion (a peripheral portion of an imaging angle of view) of a screen is not desirable. Therefore, it is desired to perform measurement (length measurement) at a central portion (a central portion of the imaging angle of view) of the screen as much as possible. Hence, it is desirable that the position where the optical axis L1 of the measurement auxiliary light crosses the optical axis L2 of the imaging optical system 130 is between the near end and the far end of the observation distance. Studies were conducted under the conditions shown in Examples 1 to 10 from such a viewpoint. Additionally, a case where the optical axis L1 of the measurement auxiliary light and the optical axis L2 of the imaging optical system 130 are parallel to each other was adopted as the comparative example as in the above-described JP1996-285541A. The results are shown in a table of FIG. 29. As criteria of evaluation, a case where the position where the optical axis L1 of the measurement auxiliary light crosses the optical axis L2 of the imaging optical system 130 is between the near end and the far end of the observation distance was "very excellent", and a case where the position was at the near end or the far end was "excellent", and a case where the position is not from the near end to the far end was "no good". As can be seen from the table of FIG. 29, as the Angle (inclination angle), a range of 1.1 degrees or more and 50.2 degrees or less degrees is preferable (evaluation is "excellent" or "very excellent", and a range of 10.5 degrees or more and 50.2 degrees or less) is more preferable (evaluation is "very excellent").

Other Embodiments

In the above-described first embodiment, the aspect in which the laser head 506 includes the GRIN lens 510 and the prism 512, and the measurement auxiliary light is the red laser light with a wavelength of 650 nm has been described. However, in the invention, the configuration of the laser head, the wavelength of the measurement auxiliary light, and the measuring processing based on these are not limited to such an aspect. Other aspects regarding the configuration of the laser head and the wavelength of the measurement auxiliary light will be described below. In addition, in the following description, the same components as those of the first embodiment will be designated by the same reference signs and the detailed description thereof will be omitted.

Second Embodiment

Although the configuration of a laser head in a second embodiment is the same as the laser head 506 related to the first embodiment, the second embodiment is different from the first embodiment in that a blue laser (semiconductor laser) in which the wavelength of the measurement auxiliary light is a wavelength of 445 nm is used. In addition, the LED may be used instead of the semiconductor laser, or the semiconductor laser may be used in an LED light emission state below an oscillation threshold value.

In the second embodiment having such a configuration, the measurement of a spot position and the creation of a marker are basically the same as those of the first embodiment. However, as described above, in the second embodiment, the blue laser is used for the measurement auxiliary light. Thus, during the measurement of the spot position, a threshold value is provided to the signal intensity of B pixels (pixel signals that are pixels in which blue color filters are disposed) of the bit map data or the RAW data to perform binarization, and the center of gravity of a white portion (a pixel having a higher signal intensity than the threshold value) is calculated. In a case the spot position is measured by an actual observation image, it is preferable that threshold values are provided to values of G signals and R signals (pixel signals of pixels in which green and red color filters are disposed, respectively), and coordinates in which the values of the G signals and the R signals that are the bit map data are equal to or smaller than the threshold values are extracted.

In the endoscopic image, there is a case where it is difficult to recognize a spot with red light because much of the digestive tract is reddish, and as in the second embodiment, there is a case where the recognition is insufficient even in a case where blue light is used. In this case, it is preferable to turn off white illumination light (visible light source 310A) in a frame (measurement mode) in which the position of a spot is measured or weaken intensity to such a degree that measurement of a spot is not affected. Meanwhile, except for a frame (normal observation mode) in which a spot is recognized, the illumination light is set to regular output to build an image. By virtue of such control of the illumination light, the recognition success rate of a spot can be markedly improved.

Third Embodiment

Next, a third embodiment of the invention will be described. Although the third embodiment is the same as that of the first above-described second embodiment in terms of the configuration of the laser head, the third embodiment is different from the first and second embodiments in that a green laser (semiconductor laser) in which the wavelength of the measurement auxiliary light is a wavelength of 505 nm is used. In addition, the LED (for example, a wavelength of 530 nm) or a solid-state laser (for example, a wavelength of 532 nm) may be used instead of the semiconductor laser, or the semiconductor laser may be used in an LED light emission state below an oscillation threshold value.

In the third embodiment having such a configuration, the measurement of a spot position and the creation of a marker are basically the same as those of the first and second embodiments. However, as described above, in the third embodiment, the green laser is used for the measurement auxiliary light. Thus, during the measurement of the spot position, a threshold value is provided to the signal intensity of G pixels (pixel signals that are pixels in which green color filters are disposed) of the bit map data or the RAW data to binarize an image, and the center of gravity of a white portion (a pixel having a higher signal strength than the threshold value) is calculated. In a case the spot position is measured by an actual observation image, it is preferable that threshold values are provided to values of B signals and R signals (pixel signals of pixels in which blue and red color filters are disposed, respectively), and coordinates in which the values of the B pixels and the R pixels that are the bit map data are equal to or smaller than the threshold values are extracted.

In the endoscopic image, there is a case where it is difficult to recognize a spot with red light because much of the digestive tract is reddish, and as in third embodiment, there is a case where the recognition is insufficient even in a case where green light is used. In this case, it is preferable to turn off white illumination light (visible light source 310A) in a frame (measurement mode) in which the position of a spot is measured or weaken intensity to such a degree that measurement of a spot is not affected. Meanwhile, except for a frame (normal observation mode) in which a spot is recognized, the illumination light is set to regular output to build an image. By virtue of such control of the illumination light, the recognition success rate of a spot can be markedly improved.

Fourth Embodiment

Figure 30:
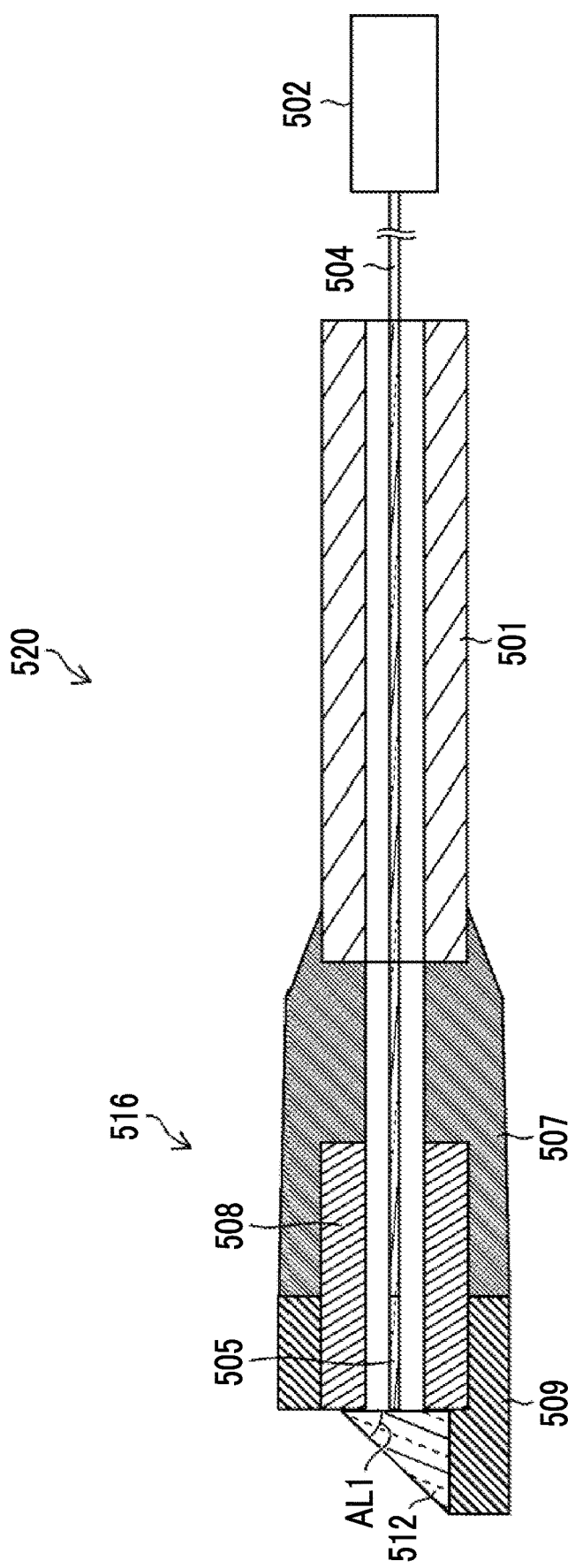
FIG. 30 is a view illustrating the configuration of a laser module related to a fourth embodiment of the invention.

Next, a fourth embodiment of the invention will be described. The fourth embodiment is different from the above-described first to third embodiments in terms of the configuration of a laser module (laser head). The configuration of a laser module 520 related to the fourth embodiment is as illustrated in FIG. 30. In a laser head 516 (head), instead of the GRIN lens 510, an optical fiber 505 (the collimator or a graded index type optical fiber) is provided on the distal end side of the optical fiber 504. The optical fiber 505 is a graded index type optical fiber of which the refractive index is at the highest on the optical axis thereof and decrease radially outward, and functions as a collimator that emits the laser light, which is guided by the optical fiber 504 and entered, as parallel light, similarly to the GRIN lens 510. The spread of the beam emitted from the optical fiber 505 can be adjusted by adjusting the length of the optical fiber 505, and (λ/4) pitch (λ is the wavelength of the laser light) or the like may be used to emit the laser light as the parallel beam.

In the fourth embodiment, the measurement auxiliary light is a red laser (semiconductor laser) of which the wavelength is a wavelength of 650 nm. In addition, the LED or the solid-state laser may be used instead of the semiconductor laser, or the semiconductor laser may be used in an LED light emission state below an oscillation threshold value. In the third embodiment having such a configuration, the measurement of a spot position and the creation of a marker can be performed similarly to the first embodiment in which the wavelength of the measurement auxiliary light is common.

Fifth Embodiment

Figure 31:
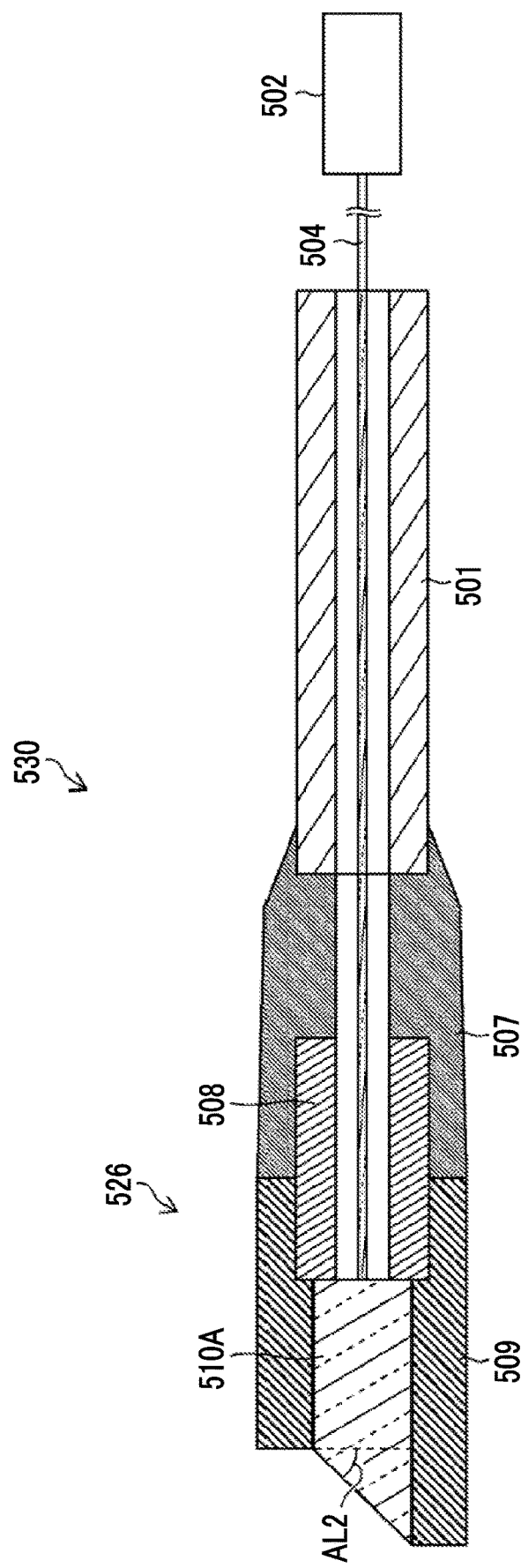
FIG. 31 is a view illustrating the configuration of a laser module related to a fifth embodiment of the invention.

Next, a fifth embodiment of the invention will be described. The fifth embodiment is different from the above-described first to fourth embodiments in terms of the configuration of a laser module (laser head). The configuration of a laser module 530 related to the fifth embodiment is as illustrated in FIG. 31, and is different in that a distal end portion of a laser head 526 (head) is not provided with a prism but is provided with a GRIN lens 510A (collimator). The GRIN lens 510A is a graded index type lens of which the refractive index is at the highest on the optical axis thereof and decrease radially outward, similarly to the GRIN lens 510 related to the first to third embodiments. However, the length of the GRIN lens 510A in the direction of the optical axis is longer than that of the GRIN lens 510 as much as a portion where no prism is provided on the distal end side. Additionally, a distal end of the GRIN lens 510A is obliquely cut, and this obliquely cut distal end portion functions as a prism. An angle AL2 of FIG. 31 corresponds to the apex angle AL1 of the prism 512 in FIGS. 5 and 30.

In the fifth embodiment, the measurement auxiliary light is the red laser (semiconductor laser) of which the wavelength is a wavelength of 650 nm. In addition, the LED or the solid-state laser may be used instead of the semiconductor laser, or the semiconductor laser may be used in an LED light emission state below an oscillation threshold value. In the fifth embodiment having such a configuration, the measurement of a spot position and the creation of a marker can be performed similarly to the first and fourth embodiments in which the wavelength of the measurement auxiliary light is common.

Also in the above-described second to fifth embodiments, the size of a subject can be easily and highly accurately measured similarly to the first embodiment.

Modification Example 1

Next, modification examples of the above-described embodiments will be described. In the above-described first to fifth embodiments, the emission angle of the measurement auxiliary light is changed by the prism 512 or the GRIN lens 510A. However, means for changing the emission angle of the measurement auxiliary light in the invention is not limited to these members. For example, as illustrated in Modification Example 1 of FIG. 32, the emission angle of the measurement auxiliary light may be changed by reflecting a laser beam B1 (measurement auxiliary light) emitted from a laser head 540, by a mirror 542 provided in front of the laser head 540 (on the distal end side of the distal end rigid part 116). In addition, in FIG. 32, reference signs L2, θ2, and L3 respectively represents an optical axis of the imaging optical system 130, an imaging field angle of the imaging optical system 130, and an optical axis of the laser beam B1.

Figure 32:
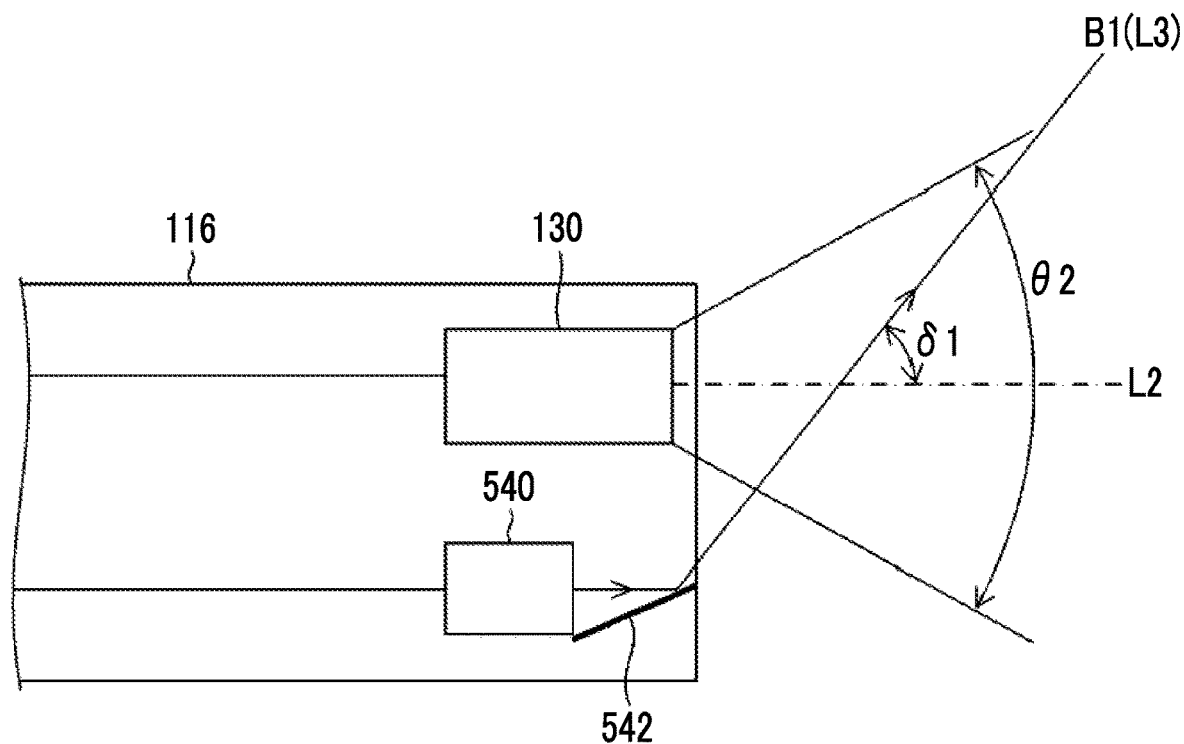
FIG. 32 is a view illustrating a state of emission angle changes of the measurement auxiliary light by a mirror.

By virtue of the above-described configuration, also in Modification Example 1 illustrated in FIG. 32, in a case where the optical axis L3 of the laser beam B1 is projected on the plane (a plane including a paper plane of FIG. 32) including the optical axis L2 of the imaging optical system 130 similarly to the above-described first to fifth embodiments, the optical axis L3 has an inclination angle δ1 that is not 0 degrees with respect to the optical axis L2, crosses the field angle of the imaging optical system 130, and intersects the optical axis L2. Accordingly, also in Modification Example 1, the size of a subject can be easily and highly accurately measured similarly to the first to fifth embodiments.

Modification Example 2

In the above-described first embodiment, since the solid prism 512 is used, the inclination angle (emission direction) of the measurement auxiliary light is constant. However, the inclination angle of the measurement auxiliary light may be configured to be changeable using a liquid prism. For example, WO2012/043211A discloses a liquid prism capable of controlling the inclination of a prism interface with respect to an optical axis by controlling an interface position between first and second liquids, and the inclination angle of the measurement auxiliary light can be changed in accordance with measurement conditions by using such a liquid prism. In addition, a relationship between the optical axis of the imaging optical system and the optical axis of the measurement auxiliary light in Modification Example 2 can be the same relationship as those of the first to fifth embodiments. Accordingly, the size of a subject can be easily and highly accurately measured similarly to the first to fifth embodiments and Modification Example 1.

Modification Example 3

Next, Modification Example 3 will be described. In the above-described first to fifth embodiments and Modification Examples 1 and 2, the emission direction of the measurement auxiliary light is changed by optical members, such as a prism, a GRIN lens, a mirror, and a liquid prism so as to have the inclination angle at which the optical axis of the measurement auxiliary light is not 0 degrees with respect to the optical axis of the imaging optical system. However, means for realizing such a state is not limited to the arrangement of the optical members. In a case where the diameter of the distal end rigid part 116 does not become a problem, as illustrated in FIG. 33, the laser head 540 can be disposed obliquely with respect to the imaging optical system 130.

Figure 33:
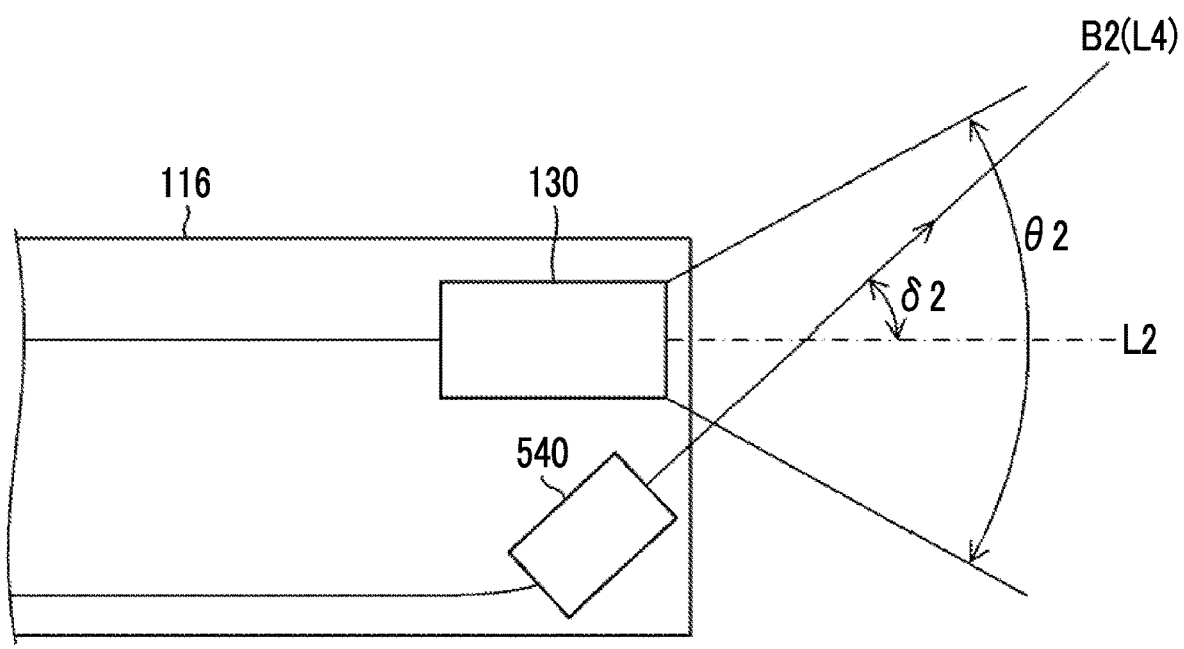
FIG. 33 is a view illustrating a state where a laser head is obliquely disposed to the imaging optical system.

Accordingly, also in Modification Example 3 illustrated in FIG. 33, in a case where an optical axis L4 of a laser beam B2 is projected on the plane (a plane including a paper plane of FIG. 33) including the optical axis L2 of the imaging optical system 130 similarly to the above-described first to fifth embodiments and Modification Examples 1 and 2, the optical axis L4 has an inclination angle δ2 that is not 0 degrees with respect to the optical axis L2, crosses the field angle of the imaging optical system 130, and intersects the optical axis L2. Accordingly, also in Modification Example 3, the size of a subject can be easily and highly accurately measured similarly to the first to fifth embodiments and Modification Examples 1 and 2.

Modification Example of Illumination Light Source

In the above-described embodiments and modification examples, a case where the light source device 300 (illumination light source) for illumination and observation includes the visible light source 310A (illumination light source), and the infrared light source 310B (illumination light source) has been described. However, in the implementation of the invention, the configuration of the light source is not limited to such an aspect. For example, the light source may be constituted of combinations of a plurality of LEDs with different wavelengths, such as white; blue, green, and red; or purple, blue, green, and red. In this case, LEDs of respective colors may be made to emit light independently, and LEDs of a plurality of colors may be made to emit light simultaneously. Additionally, white light may be radiated by making the LEDs of all the colors emit light simultaneously.

Additionally, the light source device may be constituted of a laser light source for the white light (broadband light) and a laser light source for narrowband light. In this case, the narrowband light can be selected from one wavelength or a plurality of wavelengths, such as blue or purple.

Additionally, the light source may be a xenon light source, and the light source device may be constituted of a light source for normal light (white light) and a light source for narrowband light. In this case, the narrowband light can be selected from one wavelength or a plurality of wavelengths, such as blue or green. For example, wavelengths of the narrowband light to be radiated may be switched by rotating a disk-shaped filter (rotary color filter) disposed in front of the light source and provided with blue and green color filters. In addition, the narrowband light may be infrared light of two or more wavelengths having different wavelengths.

It is preferable that the light source type of the light source device, the wavelengths, and the presence or absence of the filters are configured in accordance with the type of subject, the purposes of observation, or the like. Additionally, it is preferable to combine and/or switch the wavelengths of the illumination light in accordance with the type of subject, the purposes of observation, or the like during observation. For example, it is preferable to appropriately combine and or switch the wavelengths of the illumination light between the above-described LED lights of respective colors, between white laser light and first and second narrowband laser lights (blue and purple), between blue narrowband light and green narrowband light or between first infrared light and second infrared light.

Modification Example of Imaging Element and Imaging Method

In the above-described embodiments and modification examples, a case where the imaging element 134 is a color imaging element in which color filters are disposed at pixels, respectively, has been described. However, in the invention, the configuration of the imaging element and the imaging method are limited to such an aspect, and a monochrome imaging element (a CCD type, a CMOS type, or the like) may be used.

In a case where the monochrome imaging element is used, images can be face-sequentially (color-sequentially) captured by sequentially switching the wavelengths of the illumination light. For example, the wavelengths of the illumination light to be emitted may be sequentially switched between purple, blue, green, and red, and the wavelengths of the illumination light to be emitted by rotary color filters (red, green, blue, and the like) may be switched by radiating the broadband light (white light). Additionally, the wavelengths of the illumination light to be emitted by rotary color filters (green, blue, and the like) may be switched by radiating one or a plurality of narrowband lights (green, blue, and the like). The narrowband light may be infrared light of two or more wavelengths having different wavelengths.

<Others>

The measurement support device, the endoscope system, the processor for an endoscope system, the measurement support method in the invention can also be applied to cases where test objects, which are not living bodies, such as a pipe, are measured in addition to measuring the test object that is a living body. Additionally, the measurement support device and the measurement support method of the invention can be applied not only to the endoscope but also to cases where the dimensions and shapes of industrial parts and products are measured.

Although the example of the invention has been described above, it is obvious that the invention is not limited to the above-described embodiments and modification examples, and various modifications can be made without departing from the spirit of the invention.

EXPLANATION OF REFERENCES

10: endoscope system
100: endoscope device
102: proximal operating part
104: insertion part
106: universal cable
108: light guide connector
110: endoscope body
112: soft part
114: bent part
116: distal end rigid part
116A: distal-end-side end surface
123: Illumination unit
123A: illuminating lens
123B: illuminating lens
126: forceps port
130: imaging optical system
132: imaging Lens
134: imaging element
136: drive circuit
138: AFE
170: light guide
200: endoscope processor
202: image Input controller
204: image processing unit
206: video output unit
208: operating Part
210: CPU
212: memory
300: light source device
310: light source
310A: visible light source
310B: infrared light source
330: stop
340: condensing lens
350: light source control unit
400: monitor 500: laser module
501: fiber outer jacket
502: laser light source module
503: condensing lens
504: optical fiber
505: optical fiber
506: laser head
507: reinforcing Member
508: ferrule
509: housing
510: GRIN lens
510A: GRIN lens
512: prism
512A: mirror plane
516: laser head
526: laser head
520: laser module
530: laser module
540: laser head
542: mirror
AL1: apex angle
B1: laser beam
B2: laser beam
IA: imaging range
L1: optical axis
L1A: optical axis
L1B: optical axis
L2: optical axis
L3: optical axis
L4: optical axis
M1 to M3: marker
M1A: marker
M3A: marker
P1: near end
P3: far end
P4 to P9: spot position
R1: range
R2: imaging range
R3: imaging range
S10 to S34: respective steps of measurement support method
SP0: spot
sp1 to sp5: spot
g1, g2: function
h1, h2: function
tm: tumor
tm1 to tm3: tumor
α: apex angle
δ1: inclination angle
δ2: inclination angle

What is claimed is:

1. A measurement support device comprising:
a head including a collimator that emits measurement auxiliary light emitted from a light source as a collimated beam;
an imaging unit that acquires an image of a subject, on which a spot is formed with the measurement auxiliary light emitted from the head, via an imaging optical system and an imaging element;
a memory that stores information indicating a relationship between each of a plurality of predetermined positions of the spot on the imaging element and a corresponding actual size of the subject, wherein the relationship is determined in advance without use of a distance measured to the subject;
a processor, configured to:
use the information indicating the relationship from the memory and a measured position of the spot on the imaging element to determine the actual size of the subject corresponding to the measured position of the spot, and create a marker indicating the corresponding actual size of the subject by obtaining a number of pixels corresponding to the marker on the imaging element; and
make a display device display the image of the subject on which the spot is formed and the marker, and the marker be displayed in the vicinity of the spot in the image of the subject,
wherein the head emits measurement auxiliary light of which an optical axis has an inclination angle that is not 0 degrees with respect to an optical axis of the imaging optical system, and crosses a field angle of the imaging optical system, in a case where the optical axis of the measurement auxiliary light is projected on a plane including the optical axis of the imaging optical system.

2. The measurement support device according to claim 1, wherein the memory stores information indicating a distortion aberration of a lens constituting the imaging optical system, and
wherein the processor causes the marker to be displayed while creating the marker on the basis of a position at which the marker is displayed and the information indicating the distortion aberration of the lens stored in the memory.

3. The measurement support device according to claim 1, wherein the optical axis of the measurement auxiliary light emitted from the head is present in the plane.

4. The measurement support device according to claim 1, wherein the optical axis of the measurement auxiliary light emitted from the head intersects the optical axis of the imaging optical system in the plane.

5. The measurement support device according to claim 1, wherein the head has an optical member that changes an emission direction of the measurement auxiliary light emitted from the collimator and that changes the emission direction of the measurement auxiliary light such that an angle formed in the plane between the optical axis of the measurement auxiliary light emitted by the head and the optical axis of the imaging optical system becomes the inclination angle.

6. The measurement support device according to claim 5, wherein the optical member is a prism member having an apex angle depending on the inclination angle.

7. The measurement support device according to claim 1, further comprising:
an optical fiber that allows the measurement auxiliary light emitted from the light source to propagate to the collimator in a single transverse mode.

8. The measurement support device according to claim 1, wherein the collimator is a graded index type lens of which a refractive index is highest on an optical axis thereof and decreases radially outward.

9. The measurement support device according to claim 1, wherein the collimator is a graded index type optical fiber of which a refractive index is highest on an optical axis thereof and decreases radially outward.

10. The measurement support device according to claim 1,
wherein the inclination angle is 1.1 degrees or more and 50.2 degrees or less in a case where the optical axis of the measurement auxiliary light is projected on the plane.

11. An endoscope system comprising:
the measurement support device according to claim 1.

12. The endoscope system according to claim 11, further comprising:
an endoscope having an insertion part to be inserted into a test object, the insertion part having a distal end rigid part and a bent part connected to a proximal end side of the distal end rigid part, and a soft part connected to a proximal end side of the bent part, and an operating part connected to a proximal end side of the insertion part,
wherein the distal end rigid part is provided with the collimator and an imaging lens for forming an optical image of the spot on the imaging element.

13. The endoscope system according to claim 11, further comprising:
an illumination light source that radiates illumination light, wherein the processor is further configured to:
control illuminance of the illumination light,
wherein the processor makes the illuminance of the illumination light in a measurement mode in which an image of the spot is acquired by the imaging unit lower than that in a normal observation mode in which the subject is observed by irradiating the subject with the illumination light.

14. The endoscope system according to claim 11,
wherein the imaging element is a color imaging element including a plurality of pixels including a plurality of two-dimensionally arranged light receiving elements, and color filters of a plurality of filter colors disposed in the plurality of pixels, and
wherein the processor measures the position of the spot on the imaging element on the basis of an image created by an image signal of a pixel in which a color filter of a filter color with the highest sensitivity to a wavelength of the measurement auxiliary light, among the plurality of filter colors, is disposed.

15. A light source driver for the endoscope system according to claim 11, the light source driver is configured to drive the light source.

16. The light source driver according to claim 15,
wherein the light source driven by the light source driver is a laser light source.

17. A measurement support method using a measurement support device including a head including a collimator that emits measurement auxiliary light emitted from a light source as a collimated beam, an imaging unit that acquires an image of a subject, on which a spot is formed with the measurement auxiliary light, via an imaging optical system and an imaging element, and a memory that stores information indicating a relationship between each of a plurality of predetermined positions of the spot on the imaging element and a corresponding actual size of the subject, wherein the relationship is determined in advance without use of a distance measured to the subject, and wherein the method comprises:
emitting the measurement auxiliary light such that an optical axis of the auxiliary light has an inclination angle that is not 0 degrees with respect to an optical axis of the imaging optical system in a case where an optical axis of the measurement auxiliary light emitted from the head is projected on a plane including the optical axis of the imaging optical system;
acquiring an image of the subject, on which the spot is formed with the measurement auxiliary light, via the imaging unit;
measuring the position of the spot on the imaging element on the basis of the image of the subject;
using the information indicating the relationship from the memory and the measured position of the spot on the imaging element to determine the actual size of the subject corresponding to the measured position of the spot, and creating a marker indicating the corresponding actual size of the subject by obtaining a number of pixels corresponding to the marker on the imaging element; and
making a display device display the image of the subject on which the spot is formed and the marker, and the marker be displayed in the vicinity of the spot in the image of the subject.

* * * * *